US011983485B2

(12) United States Patent
Breber et al.

(10) Patent No.: US 11,983,485 B2
(45) Date of Patent: May 14, 2024

(54) SYSTEM FOR CONFIGURING A NATURAL-LANGUAGE MEDICAL RECORD GENERATION PLATFORM

(71) Applicant: Augmedix Operating Corporation, San Francisco, CA (US)

(72) Inventors: Sandra Breber, Orinda, CA (US); Sarah Niehaus, Ross, CA (US); Nathanael Wolfe, Oakland, CA (US); Patrick Cameron, Oakland, CA (US); Md Habibullah Al Hadi, Calgary (CA)

(73) Assignee: Augmedix Operating Corporation, San Francisco, CA (US)

( * ) Notice: Subject to any disclaimer, the term of this patent is extended or adjusted under 35 U.S.C. 154(b) by 15 days.

(21) Appl. No.: 17/313,540

(22) Filed: May 6, 2021

(65) Prior Publication Data

US 2021/0390249 A1    Dec. 16, 2021

Related U.S. Application Data

(60) Provisional application No. 63/038,498, filed on Jun. 12, 2020, provisional application No. 63/038,479, filed on Jun. 12, 2020.

(51) Int. Cl.
*G06F 3/0484* (2022.01)
*G06F 3/0482* (2013.01)
(Continued)

(52) U.S. Cl.
CPC .......... *G06F 40/166* (2020.01); *G06F 3/0482* (2013.01); *G06F 3/0484* (2013.01);
(Continued)

(58) Field of Classification Search
CPC ........ G16H 10/60; G16H 70/00; G16H 20/10; G06F 3/0482; G06F 3/0484;
(Continued)

(56) References Cited

U.S. PATENT DOCUMENTS 5,267,155 A * 11/1993 Buchanan ............. G06F 40/174
715/210
8,612,261 B1    12/2013 Swanson et al.
(Continued)

FOREIGN PATENT DOCUMENTS

CN    107633876 A    1/2018
CN    108447534 A    8/2018

OTHER PUBLICATIONS

Duke et al. (2014). "Regenstrief Institute's Medical Gopher: A next-generation homegrown electronic medical record system," International Journal of Medical Informatics (83): 170-179.
(Continued)

*Primary Examiner* — Dino Kujundzic
(74) *Attorney, Agent, or Firm* — Morrison & Foerster LLP

(57) ABSTRACT

Systems and methods for configuring a medical record generation platform are provided. A first graphical user interface comprising a visual representation of a natural-language statement structure is displayed, and a first input comprising an instruction to update the natural-language statement structure to specify a first aspect of patient medical information is received. In response to receiving the first input, display of the visual representation is updated to include a visual representation of the first aspect of patient medical information, and an option group region representing a set of options for describing the first aspect is displayed. In accordance with the first user input, a data structure is stored comprising instructions for providing a platform for generating a natural-language healthcare document conforming to the natural-language statement structure represented by the visual representation, wherein the natural-language statement specifies the first aspect of patient medical information.

27 Claims, 17 Drawing Sheets

(51) Int. Cl.
   *G06F 40/166* (2020.01)
   *G06F 40/40* (2020.01)
   *G16H 10/60* (2018.01)
   *G16H 20/10* (2018.01)

(52) U.S. Cl.
   CPC ............. *G06F 40/40* (2020.01); *G16H 10/60* (2018.01); *G16H 20/10* (2018.01); *G06F 2203/04803* (2013.01)

(58) Field of Classification Search
   CPC ....... G06F 3/04847; G06F 2203/04803; G06F 40/166; G06F 40/56
   See application file for complete search history.

(56) References Cited

U.S. PATENT DOCUMENTS

| | | | |
|---|---|---|---|
| 10,541,053 B2 | 1/2020 | Sheffer et al. | |
| 10,949,602 B2 | 3/2021 | Snider et al. | |
| 11,024,424 B2* | 6/2021 | Sun | G06K 9/6218 |
| 11,348,689 B1* | 5/2022 | Gonzales, Jr. | G06F 3/04817 |
| 2003/0220819 A1* | 11/2003 | Burstein | G06Q 10/10 705/3 |
| 2011/0040576 A1* | 2/2011 | Madan | G06Q 10/10 705/3 |
| 2011/0078570 A1* | 3/2011 | Larsen | G16H 10/60 715/710 |
| 2011/0238446 A1 | 9/2011 | Chaudhry | |
| 2012/0290310 A1* | 11/2012 | Watson | G16H 10/60 706/50 |
| 2013/0024382 A1 | 1/2013 | Dala et al. | |
| 2015/0178874 A1* | 6/2015 | Harris | G16H 40/20 705/3 |
| 2016/0364532 A1* | 12/2016 | Honeycutt | G16H 40/20 |
| 2017/0061093 A1 | 3/2017 | Amarasingham et al. | |
| 2017/0147751 A1 | 5/2017 | Schwartz et al. | |
| 2017/0213005 A1 | 7/2017 | Cox et al. | |
| 2017/0220757 A1 | 8/2017 | Cox et al. | |
| 2017/0220758 A1 | 8/2017 | Cox et al. | |
| 2017/0235886 A1 | 8/2017 | Cox et al. | |
| 2017/0235888 A1 | 8/2017 | Rahman et al. | |
| 2017/0235906 A1 | 8/2017 | Dorris et al. | |
| 2017/0277854 A1 | 9/2017 | Kelly et al. | |
| 2017/0278209 A1 | 9/2017 | Olsen et al. | |
| 2017/0364640 A1* | 12/2017 | Badawi | G16H 70/00 |
| 2018/0232489 A1 | 8/2018 | Fink et al. | |
| 2018/0373844 A1* | 12/2018 | Ferrandez-Escamez | G16H 50/20 |
| 2019/0122750 A1* | 4/2019 | Ghosh | G16H 10/40 |
| 2020/0237452 A1 | 7/2020 | Wolf et al. | |
| 2021/0303630 A1* | 9/2021 | Atkinson | G06F 16/9038 |
| 2021/0390265 A1 | 12/2021 | Breber et al. | |
| 2022/0084645 A1 | 3/2022 | Ginsburg et al. | |
| 2022/0084664 A1 | 3/2022 | Ginsburg | |

OTHER PUBLICATIONS

Kaufman et al. (2016). "Natural Language Processing-Enabled and Conventional Data Capture Methods for Input to Electronic Health Records: A Comparative Usability Study," JMIR Med Inform 4(4): 1-20.

Lin et al. (2015). "Comparison of a semi-automatic annotation tool and a natural language processing application for the generation of clinical statement entries," American Medical Informatics Association 22: 132-142.

Minock et al. "Towards Building Robust Natural Language Interfaces to Databases," 13th International Conference on Applications of Natural Language to Information Systems, Jun. 24-27, 2008, London, UK; pp. 187-198.

Taira et al. (1999). "A Statistical Natural Language Processor for Medical Reports," AMIA Inc.: 970-974.

Wallace et al. (Jun. 2012). "Closing the Gap between Methodologists and End-Users: R as a Computational Back-End," Journal of Statistical Software 49(5): 1-15.

Breber et al., U.S. Office Action dated Jun. 13, 2022, directed to U.S. Appl. No. 17/313,482; 15 pages.

Breber et al., U.S. Office Action dated Nov. 25, 2022, directed to U.S. Appl. No. 17/313,482; 21 pages.

Breber et al., U.S. Office Action dated May 25, 2023, directed to U.S. Appl. No. 17/313,482; 18 pages.

* cited by examiner

FIG. 2C

Notebuilder - Step 3: "Review"

≡ Notewriter | Trainee Sydee Teel Primary (PC), 0 other ▾ | Sign out | Connected with sarah niebaus | Disconnect Yesterday, Tue, May 19th 2020 ▾

Danny Patterson — Expires in 2 days
Jane Smith — Expires in 2 days
John Doe — Expires in 2 days
Don Donaldson — Expires in 2 days
Martin Day — Expires in 2 days NAME Danny Patterson Templates ▾ | Uploaded files ▾ | Scheduled ▾ | 🗎 Save note | START 11:05 AM | END 11:35 AM | Initiate recap | ⊘ Not connected ▾

The patient is a 24 year old male presenting today for: Abdominal pain.

GI symptoms
The patient's symptoms include nausea, vomiting and abdominal pain, but do not include diarrhea or decreased appetite. He reports sudden onset 5 days ago. Context includes recent antibiotic use and recent travel. Patient was cave diving in Belize He rates severity as severe. Aggravating factors include moving and lying down. Alleviating factors include lying down, but do not include sitting or standing. The patient's medical history is significant for Crohn's Disease and narcotics use.

Hyperlipidemia
Status is uncontrolled. Current diet is low fat and medium fat. His exercise routine includes extensive walking, medication regimen : Tylenol.

Review of Systems
Constitutional: Negative for fevers, chills, sweats.
Skin: Negative for rash, erythema, lesions.
Eyes: Negative for eye pain, eye redness, itching, vision changes, diplopia.
ENT: Negative for otalgia, rhinorrhea, sore throat.
Cardiovascular: Negative for chest pain, palpitations.
Respiratory: Negative for dyspnea, cough, wheezing, orthopnea.
Gastrointestinal: Negative for abdominal pain, nausea, vomiting, diarrhea, constipation.
Genitourinary: Negative for dysuria, hematuria, frequent urination, retention, hesitancy, genital lesions, dyspareunia.
Musculoskeletal: Negative for back pain, neck pain, joint pain.
Neurological: Negative for dizziness, headache, numbness, tingling.
Psychiatric: Negative for depression, anxiety, hallucinations, suicidal ideation, homicidal ideation.
Endocrine/Hematologic: Negative for polyuria, polydipsia, hot flashes, hair loss, easy bruising.

Physical Exam
General: Well appearing and in no acute distress.
HEENT: PERRL, EOMI, conjunctiva clear, TMs clear, oropharynx clear without erythema or exudates.
Cardiovascular: Regular rate and rhythm. No murmur, rub or gallop.
Respiratory: Clear to auscultation bilaterally. No wheezes, rales, or rhonchi.
Psychiatric: Normal mood and affect Assessment and Plan Provider offline ● Provider offline Message to provider
Enter a message for provider No card logs available Audio
0 To review  0 Archived

FIG. 5C ically) after their creation and storage. Additionally, there is a need for improved systems, methods, and/or user interfaces for configuring platforms for creating electronic health records, including by using back-end user interfaces to flexibly configure front-end user interfaces for collecting patient medical information for the creation of electronic health records.

SYSTEM FOR CONFIGURING A NATURAL-LANGUAGE MEDICAL RECORD GENERATION PLATFORM

CROSS-REFERENCE TO RELATED APPLICATIONS

This application claims benefit of priority of U.S. Provisional Patent Application No. 63/038,479, filed Jun. 12, 2020, and of U.S. Provisional Patent Application No. 63/038,498, filed Jun. 12, 2020, the entire contents of each of which are hereby incorporated by reference.

FIELD

This disclosure relates generally to electronic health record systems, and more specifically to user interfaces for automatically generating natural-language entries for electronic health records.

BACKGROUND

Creating electronic health records is a vital part of providing and documenting medical care across all medical fields and specialties. According to known techniques, medical practitioners manually write notes describing consultations with patients in order to record the patient's demographic information, prior medical information, previously-prescribed medication information, complaint and symptom information, and information regarding any treatment, tests, or medication prescribed for the patient during the consultation.

SUMMARY

As described above, notes regarding consultations with patients are created for electronic health records by being manually written by a medical practitioner. However, said known techniques are time-consuming and labor-intensive. Furthermore, manually creating notes for electronic medical records is prone to human error. Additionally, manually creating notes for electronic medical records may produce notes that are not in any standardized format and may therefore be poorly suited for future manual review/analysis and/or for future automated review/analysis.

Accordingly, there is a need for improved systems, methods, and/or user interfaces for creating electronic health records. Particularly, there is a need for improved systems, methods, and/or user interfaces for creating natural-language entries (e.g., notes) for storage in electronic health records in a manner that is fast, efficient, resistant to user error, flexible, configurable, and scalable. Furthermore, there is a need for said systems, methods, and/or user interfaces for creating natural-language entries (e.g., notes) for storage in electronic health records in a manner that encourages consistency of structure and content of the generated entries, such that the entries may be efficiently and accurately reviewed (whether manually or programmatically) after their creation and storage. Additionally, there is a need for improved systems, methods, and/or user interfaces for configuring platforms for creating electronic health records, including by using back-end user interfaces to flexibly configure front-end user interfaces for collecting patient medical information for the creation of electronic health records.

Disclosed herein are various systems, methods, computer-readable storage media, platforms, and graphical user interfaces that may address one or more of the above-identified needs. In some embodiments, the systems and methods disclosed herein may provide user interfaces for automatically generating natural-language entries for electronic health records. A computerized system may provide a front-end graphical user interface configured to be used by a medical professional or by a medical record management specialist to record patient medical information, such as information about a patient consultation. The interface includes a canvas portion and a menu portion, wherein the menu portion provides a plurality of graphical objects representing options that the user may select (or deselect) to indicate medical information about a patient. The indicated medical information may pertain to any aspect of patient medical information, such as a symptom, onset mode of a symptom, onset timing of a symptom, frequency (e.g., of a symptom), location of a symptom, contextual information, quality of a symptom, a prior medical condition, a current medication, a medication to be prescribed, a treatment to be prescribed, lab test results, a lab test to be ordered, imaging procedure results, an imaging procedure to be ordered, an organ system, a diagnostic procedure, a diagnosis, and/or a treatment. Based on the options selected and/or information indicated by the user in one or more fields in the menu section, the system automatically generates a natural language sentence summarizing the information indicated by the user, and the natural language sentence is displayed in the canvas section of the graphical user interface. The menu options provided to the user and the structure of the automatically generated sentences/paragraphs may be based on a template selected by the user, wherein different available templates may be associated with different patient complains and/or different medical setting and use cases.

In some embodiments, the systems and methods disclosed herein may provide back-end user interfaces for creating, configuring, and deploying the front-end user interfaces and other aspects of the platforms described herein. A back-end user interface may include a visual representation of a natural-language statement structure in addition to a visual representation of one or more options corresponding to a sentence-part of the visual representation of the natural-language statement structure. A user of the back-end user interface may execute inputs to configure the visual representation of the natural-language statement structure and may add or remove options to the set of displayed options corresponding to the sentence-part. The back-end user may thus define both a natural language statement structure and a set of options for potential integration into a natural-language statement created based on said sentence structure. The system may configure and deploy a front-end user interface based on the back-end user's inputs, wherein the front-end user interface is configured to (a) display the options selected by the back-end user for optional selection by the front-end user and to (b) generate a natural-language statement based on the options selected by the front-end user and in accordance with the natural-language sentence structure specified by the back-end user.

In some embodiments, a system for generating a natural-language statement for a healthcare record is provided, the system comprising one or more processors configured to cause the system to: display a graphical user interface comprising a canvas region and a menu region, wherein menu region comprises a first set of one or more interactive graphical user interface menu objects configured to receive user inputs corresponding to medical information; and receive data representing a first user input comprising user interaction with one or more of the first set of menu objects, the first input indicating medical information for a patient; in accordance with the first user input: generate a natural-language statement based on the medical information indicated by the first user input; and update display of the canvas region to display the natural-language statement.

In some embodiments, a non-transitory computer-readable storage medium storing instructions for generating a natural-language statement for a healthcare record is provided, the instructions configured to be executed by a system comprising one or more processors to cause the system to: display a graphical user interface comprising a canvas region and a menu region, wherein menu region comprises a first set of one or more interactive graphical user interface menu objects configured to receive user inputs corresponding to medical information; and receive data representing a first user input comprising user interaction with one or more of the first set of menu objects, the first input indicating medical information for a patient; in accordance with the first user input: generate a natural-language statement based on the medical information indicated by the first user input; and update display of the canvas region to display the natural-language statement.

In some embodiments, a method for generating a natural-language statement for a healthcare record is provided, the method performed at a system comprising one or more processor, the method comprising: displaying a graphical user interface comprising a canvas region and a menu region, wherein menu region comprises a first set of one or more interactive graphical user interface menu objects configured to receive user inputs corresponding to medical information; and receiving data representing a first user input comprising user interaction with one or more of the first set of menu objects, the first input indicating medical information for a patient; in accordance with the first user input generating a natural-language statement based on the medical information indicated by the first user input; and updating display of the canvas region to display the natural-language statement.

In some embodiments, a system for configuring a medical record generation platform is provided, the system comprising one or more processors configured to cause the system to: display a first graphical user interface comprising a visual representation of a natural-language statement structure; receive a first input comprising an instruction to update the natural-language statement structure to specify a first aspect of patient medical information; in response to receiving the first input: update display of the visual representation of the natural-language statement to include a visual representation of the first aspect of patient medical information; display an option group region configured to represent a first set of options for describing the first aspect of patient medical information; in accordance with the first user input, store a data structure comprising instructions for providing a platform for generating a natural-language healthcare document conforming to the natural-language statement structure represented by the visual representation, wherein the natural-language statement specifies the first aspect of patient medical information.

In some embodiments, a non-transitory computer-readable storage medium storing instructions for configuring a medical record generation platform is provided, the instructions configured to be executed by a system comprising one or more processors to cause the system to: display a first graphical user interface comprising a visual representation of a natural-language statement structure; receive a first input comprising an instruction to update the natural-language statement structure to specify a first aspect of patient medical information; in response to receiving the first input: update display of the visual representation of the natural-language statement to include a visual representation of the first aspect of patient medical information; display an option group region configured to represent a first set of options for describing the first aspect of patient medical information; in accordance with the first user input, store a data structure comprising instructions for providing a platform for generating a natural-language healthcare document conforming to the natural-language statement structure represented by the visual representation, wherein the natural-language statement specifies the first aspect of patient medical information.

In some embodiments, a method for configuring a medical record generation platform is provided, the method performed at a system comprising one or more processors, the method comprising: display a first graphical user interface comprising a visual representation of a natural-language statement structure; receive a first input comprising an instruction to update the natural-language statement structure to specify a first aspect of patient medical information; in response to receiving the first input: update display of the visual representation of the natural-language statement to include a visual representation of the first aspect of patient medical information; display an option group region configured to represent a first set of options for describing the first aspect of patient medical information; in accordance with the first user input, store a data structure comprising instructions for providing a platform for generating a natural-language healthcare document conforming to the natural-language statement structure represented by the visual representation, wherein the natural-language statement specifies the first aspect of patient medical information.

In some embodiments, a system for configuring a medical record generation platform is provided, the system comprising one or more processors configured to cause the system to: store a data structure comprising instructions for providing a platform for generating natural-language healthcare records, wherein providing the platform comprises: causing display of a graphical user interface comprising a set of options selectable by users of the graphical user interface; and collecting metadata regarding selection of one or more of the options by a plurality of users; and in response to collecting the metadata, update the data structure in accordance with the selection of the one or more of the options by the plurality of users.

In some embodiments, a non-transitory computer-readable storage medium storing instructions for configuring a medical record generation platform is provided, the instructions configured to be executed by a system comprising one or more processors to cause the system to: store a data structure comprising instructions for providing a platform for generating natural-language healthcare records, wherein providing the platform comprises: causing display of a graphical user interface comprising a set of options selectable by users of the graphical user interface; and collecting metadata regarding selection of one or more of the options by a plurality of users; and in response to collecting the metadata, update the data structure in accordance with the selection of the one or more of the options by the plurality of users.

In some embodiments, a method for configuring a medical record generation platform is provided, the method performed at a system comprising one or more processors, the method comprising: storing a data structure comprising instructions for providing a platform for generating natural-language healthcare records, wherein providing the platform comprises: causing display of a graphical user interface comprising a set of options selectable by users of the graphical user interface; and collecting metadata regarding selection of one or more of the options by a plurality of users; and in response to collecting the metadata, updating the data structure in accordance with the selection of the one or more of the options by the plurality of users.

BRIEF DESCRIPTION OF THE FIGURES

Various embodiments are described with reference to the accompanying figures, in which:

FIGS. 2A-2D depict respective screens of a graphical user interface of a natural-language medical record generation platform, in accordance with some embodiments.

FIGS. 4A-4B depict respective screens of a graphical user interface of a natural-language medical record generation platform, in accordance with some embodiments.

FIGS. 5A-5F depict respective screens of a graphical user interface of a system for configuring a natural-language medical record generation platform, in accordance with some embodiments.

DETAILED DESCRIPTION

Figure 1:
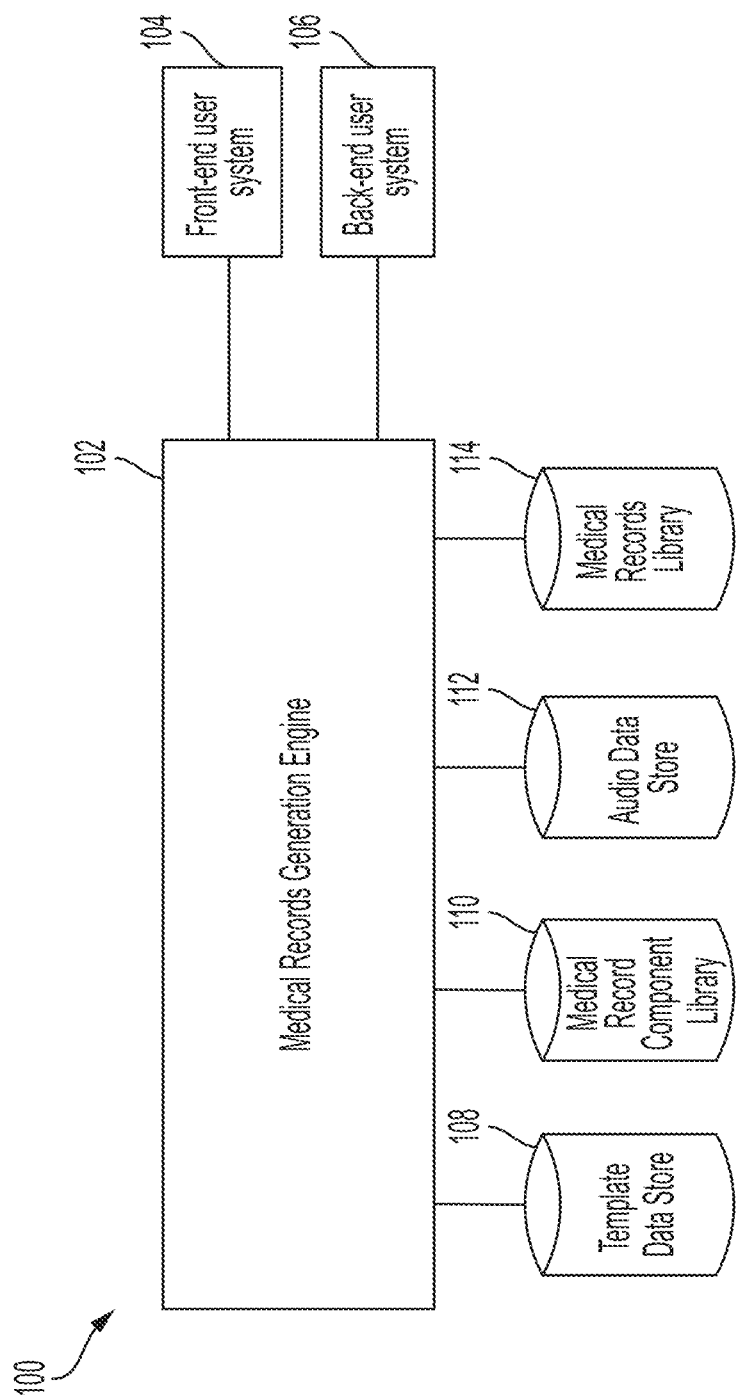
FIG. 1 depicts a system for providing a natural-language medical record generation platform, in accordance with some embodiments.

As described above and in further detail below, the disclosure herein pertains to various systems, methods, computer-readable storage media, platforms, and/or graphical user interfaces for automatically generating natural-language entries for electronic health records. A computerized system, for example as described below with reference to FIG. 1, may provide a front-end graphical user interface configured to be used by a medical professional or by a medical record management specialist to record patient medical information, such as information about a patient consultation. The system may, in some embodiments, be accessed by front-end users such as medical practitioners and/or medical records specialists (e.g., personnel tasked with creating and/or recording medical records). The system may be provided, in some embodiments, as locally-hosted software and/or by one or more servers providing the platform and graphical user interface via a network system (including by providing a GUI as part of a dedicated program/application and/or through a web-browser interface).

The graphical user interface provided to the front-end user, for example as described below with reference to FIGS. 3A-3D, may include a canvas portion and a menu portion, wherein the menu portion provides a plurality of graphical objects representing options that the user may select (or deselect) to indicate medical information about a patient. The indicated medical information may pertain to any aspect of patient medical information, such as a symptom, onset mode of a symptom, onset timing of a symptom, frequency (e.g., of a symptom), location of a symptom, contextual information, quality of a symptom, a prior medical condition, a current medication, a medication to be prescribed, a treatment to be prescribed, lab test results, a lab test to be ordered, imaging procedure results, an imaging procedure to be ordered, an organ system, a diagnostic procedure, and/or a diagnosis. Based on the options selected and/or information indicated by the user in one or more fields in the menu section, the system may automatically generate a natural language sentence summarizing the information indicated by the user, and the natural language sentence may be displayed in the canvas section of the graphical user interface.

The menu options provided to the user and the structure of the automatically generated sentences/paragraphs may be based on a template selected by the user, wherein different available templates may be associated with different patient complains and/or different medical setting and use cases. Various templates may define different options available for user selection via the GUI and may further define the natural-language sentence structure, paragraph structure, and/or document structure of the generated natural-language statements. Templates may be configured by back-end users (e.g., system administrators) and provided to front-end via locally-stored template data and/or template data provided via network communication (e.g., through a web-provided service).

As described above and in further detail below, the disclosure herein further pertains to systems, methods, and/or user interfaces for configuring platforms for creating electronic health records, including by using back-end user interfaces to flexibly configure front-end user interfaces for collecting patient medical information for the creation of electronic health records. Back-end user interfaces may be provided for creating, configuring, and deploying the front-end user interfaces and other aspects of the platforms described herein. A back-end user interface may include a visual representation of a natural-language statement structure in addition to a visual representation of one or more options corresponding to a sentence-part of the visual representation of the natural-language statement structure. A user of the back-end user interface may execute inputs to configure the visual representation of the natural-language statement structure and may add or remove options to the set of displayed options corresponding to the sentence-part. The back-end user may thus define both a natural language statement structure and a set of options for potential integration into a natural-language statement created based on said sentence structure. The system may configure and deploy a front-end user interface based on the back-end user's inputs, wherein the front-end user interface is configured to (a) display the options selected by the back-end user for optional selection by the front-end user and to (b) generate a natural-language statement based on the options selected by the front-end user and in accordance with the natural-language sentence structure specified by the back-end user.

FIG. 1 depicts a system 100 for providing a natural-language medical record generation platform, in accordance with some embodiments.

As shown in FIG. 1, system 100 may include medical records generation engine 102, front-end user system 104, backend user system 106, template data store 108, medical record component library 110, audio data store 112, and medical record library 114. As shown, each of the components of system 100 may be communicatively coupled (e.g., by wired and/or wireless electronic communication) with engine 102. In some embodiments, system 100 may be provided as a distributed (e.g., network) system with one or more components located remotely from one another and connected via network (e.g., wide-area network) communication. In some embodiment system 100 may be provided as a local system with one or more components located together with one another and connected via local network communication. In some embodiments, one or more components of system 100 may be provided as part of a single computer device. As explained herein, system 100 may provide a platform by which a front-end user of system 104 may be provided with one or more GUI's as described herein to generate and store natural-language entries for electronic health records.

Medical records generation engine 102 may comprise any one or more processors (located locally and/or remotely from front-end system 104 and/or back-end system 106) configured to perform all or part of any of the techniques disclosed herein. In some embodiments, engine 102 may be provided, in whole or in part, as one or more processors of a personal computer, laptop computer, tablet, mobile electronic device, server, distributed computing system, and/or cloud computing system.

Engine 102 may be configured to provide one or more graphical user interfaces (e.g., the interface described below with respect to FIGS. 3A-3D) to front-end users of the system such that the front-end users may supply information to system 100 regarding a patient medical consultation. For example, engine 102 may provide instructions for providing one or more graphical user interface screens to system 104 such that system 104 may display a graphical user interface and receive user inputs via said graphical user interface.

Engine 102 may then receive (via wired or wireless electronic transmission) data transmitted from front-end user system 104 regarding the user inputs detected by system 104. Based on the data received regarding front-end user input, engine 102 may generate a natural-language statement for entry into an electronic health record, wherein the natural language statement may describe one or more aspects of the patient consultation corresponding to the executed front-end user inputs. For example, the natural language statement may describe patient demographic information, patient background information, patient medical/family history information, patient complaint information, patient symptom information, patient preexisting/past medication information, patient preexisting/past treatment information, medication prescription information, test/analysis prescription information, and/or treatment prescription information. A natural-language phrase, sentence, or paragraph may be automatically generated based on a natural-language phrase structure, sentence structure, and/or paragraph structure accessible to engine 102 (e.g., stored as part of a template data structure on template data store 108). Once the natural-language statement is generated, the statement may be stored (e.g., as part of an electronic health record in medical records library 114) and/or displayed to a user (e.g., by being transmitted to front-end user system 104 for display on a display).

Front-end user system 104 may comprise any one or more computer systems (located locally and/or remotely from engine 102) configured to receive instructions and/or transmitted data from engine 102, to render and/or display a graphical user interface to a front-end user, to detect one or more inputs executed against the graphical user interface by the user, and to transmit data regarding detected user inputs to engine 102. In some embodiments, front-end user system 104 may include any suitable display and any suitable input device (e.g., mouse, keyboard, touch-sensitive device, touch-screen, microphone, etc.). In some embodiments, front-end user system 104 may be provided, in whole or in part, as a personal computer, workstation computer, laptop computer, tablet, or mobile electronic device.

Back-end user system 106 may comprise any one or more computer systems (located locally and/or remotely from engine 102) configured to send data to and/or receive data from engine 102. In some embodiments, back-end system 106 may be configured to send instructions to engine 102 in order to configure the user interface to be provided to front-end system 104, such as by configuring options to be presented to front-end users of the interface and/or configuring natural-language sentence structures and/or paragraph structures to be used to create medical notes. In some embodiments, back-end system 106 may be configured to receive transmissions from engine 102 regarding monitoring front-end users, system performance, system characteristics, and/or metadata collected based on use of the platform and graphical user interfaces by one or more front-end users. In some embodiments, back-end user system 106 may include any suitable display and any suitable input device (e.g., mouse, keyboard, touch-sensitive device, touch-screen, microphone, etc.). In some embodiments, back-end user system 106 may be provided, in whole or in part, as a personal computer, workstation computer, laptop computer, tablet, or mobile electronic device.

In some embodiments, template data store 108 may comprise any one or more computer-readable storage mediums configured to store template data. Template data may include data (e.g., one or more data structures) configured to be usable by engine 102 to provide all or part of the contents of a GUI to a user of front-end user device 104. In some embodiments, templates may govern what options are displayed to a front-end user of the system and the manner in which they are displayed to the user, as well as governing the manner in which the system generates natural-language statements based on user inputs. In some embodiments, template data store 108 may store different templates for different use cases, including different medical specialties, different languages, different countries, different regions, different states, different medical facilities, different doctors, different patient characteristics or classes, and/or different complaint types. In some embodiments, a front-end user may select an appropriate template based on the nature of the patient consultation (e.g., based on the purpose of the patient visit and/or what the patient's complaint is), and the selected template may cause the system to display appropriate and relevant options for such a consultation.

In some embodiments, templates stored in template data store 108 may be created, updated/modified, and/or deleted by system 100. In some embodiments, a back-end user of system 106 may create, modify, or delete a template by executing inputs comprising instructions to do so to system 108. In some embodiments, system 108 and/or system 100 may automatically update a template based on metadata collected regarding use of the template by one or more front-end users (e.g., if an option in the template is rarely selected, the option may be deprioritized in the template such that it is presented in a less prominent manner (e.g., further down in a list); or, if an option that is not automatically presented in a template is frequently manually added by users of the template, then the option may be added to the template such that it is automatically presented in the future).

In some embodiments, medical record component library 110 may comprise any one or more computer-readable storage mediums configured to store component information that may be used in the creation of electronic health records and/or in the creation of templates for use in the systems described herein. For example, medical record component library 110 may store data pertaining to medical specialty information, patient visit type information, patient complaint type information, complaint-element information, descriptor information (e.g., information regarding options that may be selected by users to characterize one or more complaint-elements), treatment information, test information, diagnosis information (e.g., diagnosis code information), imaging information, medications information, and/or health systems information.

The data stored in library 110 may in some embodiments be used to create (e.g., incorporated into) and/or referenced by (e.g., the system may execute a call to read the data in library 110) a template executed by the system to provide a graphical user interface for a front-end user. For example, a template may be configured to provide a plurality of options to a front-user for specifying what treatments are being prescribed to a patient; the options for the template may be populated by being automatically drawn from one or more lists or sets of treatment information stored in library 110. In some embodiments, a template may populate a set of options based on an entire dataset or an entire data subset from library 110; in some embodiments, a template may populate a set of options based on a selection of specific data items from library 110, such as items specified by a back-end user of system 108 in creating the template.

In some embodiments, audio data store 112 may comprise any one or more computer-readable storage mediums configured to store audio data. In some embodiments, audio data may be used to provide one or more user inputs, for example by using NLP to translate for conversation to inputs, and/or to copy/paste dictations using one or more speech-to-text tools. In some embodiments, inputs for the system may be user-generated and/or may be audio-generated using one or more NLP models.

In some embodiments, medical record library 114 may comprise any one or more computer-readable storage mediums configured to store medical records data such as electronic health records. In some embodiments, medical records data stored on library 114 may include natural-language medical record entry data (e.g., notes) generated by engine 102 in accordance with one or more of the technique described herein.

FIGS. 2A-2D depict respective screens 200a-200d of graphical user interface 200 of a natural-language medical record generation platform, in accordance with some embodiments. In some embodiments, GUI 200 may be displayed by a display of front-end user system 104 of system 100, such that a user of GUI 200 may execute inputs via GUI 200 in order to cause system 100 generate a natural-language entry (e.g., a note) pertaining to a patient consultation for storage as part of an electronic health record. For the purposes of the description of FIGS. 2A-2D herein, a front-end user entering information into interface 200 regarding a patient consultation may be referred to either as a user or as a "scribe." Various functionalities of the systems and platforms disclosed herein are described below with reference to GUI screens 200a-200d.

Figure 2A:
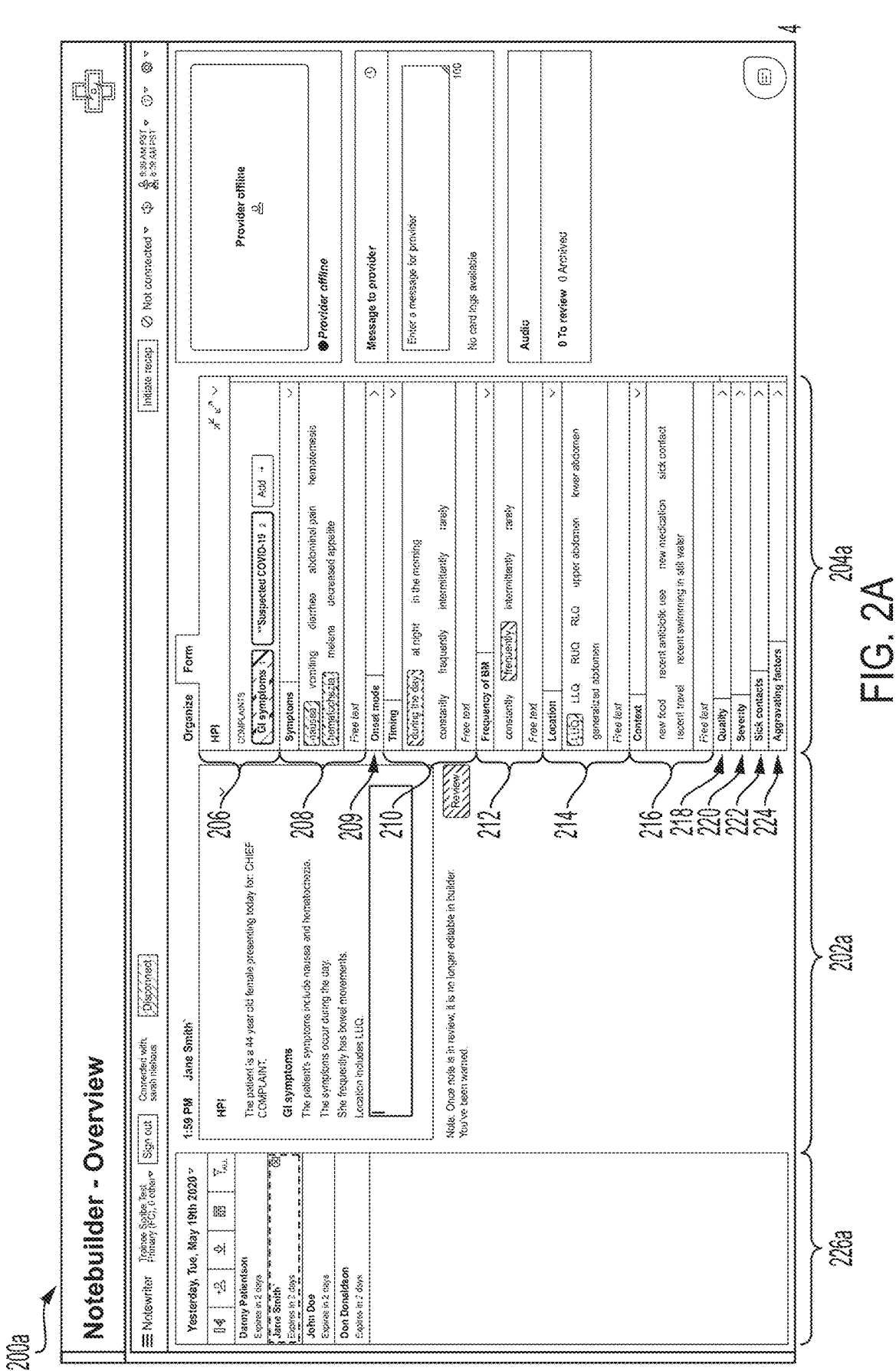

FIG. 2A depicts screen 200a of graphical user interface 200, in accordance with some embodiments. Screen 200a depicts GUI 200 during the process of capturing patient information during a patient consultation, and the description of screen 200a below provides an overview of certain functionalities of the systems and platforms disclosed herein. As shown in FIG. 2A, screen 200a comprises canvas region 202a and menu region 204a.

In some embodiments, canvas region 202a is a region of GUI 200 on which natural-language phrases, sentences, and/or paragraphs are generated based on user inputs that are executed via GUI 200. As shown in the example of FIG. 2A, canvas region 202a displays a natural-language sentence describing patient demographic information and including a placeholder for the patient's chief complaint (the placeholder may be replaced by a statement of the patient's chief complaint once an option indicating the chief complaint is selected or otherwise indicated by a user/scribe). As shown further in region 202a, region 202a displays four natural-language statements regarding the patient's complaint for GI symptoms. The natural-language statements regarding demographic information and those regarding complaint information may be generated and dynamically updated for display in canvas region 202a in real-time based on options selected and/or information inputted by the user to menu region 204a, described below in additional detail. By updating canvas region 202a in real-time, a user may receive immediate feedback regarding how selection of one or more options will affect the creation of a natural-language statement for entry into a medical record.

In some embodiments, menu region 204a is a region of GUI 200 on which a menu of various GUI objects representing various options are displayed to the user. The GUI objects displayed in menu region 202a may include one or more of the following: selectable and/or buttons/icons, drop-down menus and/or scrollable menus, character entry fields, and/or number entry fields. As shown by the examples in region 204a in screen 200a, the various GUI objects in region 202a may be configured to allow a user of GUI 200 to indicate various information about the patient consultation, including by typing in information into a field, selecting an option from a menu, and/or selecting or deselecting a button/icon option.

As shown by the examples in menu region 204a in screen 200a, GUI objects in menu region 204a may be used to indicate various aspect of information regarding a patient's complaint. In some embodiments, GUI objects may be arranged within menu region 204a into a plurality of sub-regions within menu region 204a. The option sub-regions within menu region 204a may include logically related options that may be used by a user to describe a certain aspect of a patient's symptoms, complaint information, demographic information, or other information.

In the example of FIG. 2A, menu region 204a includes complaints sub-region 206a, symptoms sub-region 208a, onset mode sub-region 209a, timing sub-region 210a, frequency sub-region 212a, location sub-region 214a, context sub-region 216a, quality sub-region 218a, severity sub-region 220a, sick contacts sub-region 222a, and aggravating factors sub-region 224a. (Other sub-regions may be included depending on the template being applied and/or in accordance with the patient, symptom, complaint, medical history, etc.) As shown, sub-regions may be displayed in a collapsed or expanded state, and a user may click or tap on a sub-region in order to toggle it between the expanded and collapsed states. In the example shown, sub-regions 206a, 208a, and 210a-216a are in an expanded state while sub-regions 209a and 218a-224a are in a collapsed state.

In some embodiments, complaints sub-region 206a may be configured to allow a user to indicate information regarding one or more complaints for a patient and/or to display one or more previously-indicated complaints. In some embodiments, a complaints sub-region may include a text entry field into which a user may type in order to search for and select one or more predefined complaint options. In the example shown in sub-region 206a, two icons show that the user has indicated a patient complaint of GI symptoms and a patient complaint of suspected COVID-19.

As further shown in sub-region 206a, a selectable "Add" icon may be selected (e.g., clicked or tapped) by a user in order to display a field allowing the user to search for and/or add one or more additional complaints. In some embodiments, one or more complaints displayed in a complaints sub-region may be pre-populated based on information entered by a user at a different screen of GUI 200 (e.g., at a setup screen or an organization screen as described below with reference to FIG. 2B).

In some embodiments, a user may be able to select (e.g., tap or click) one of the GUI objects (e.g., icons) representing a complaint in order to cause GUI 200 to display one or more other sub-regions and/or GUI objects associated with the selected complaint. In the example shown in FIG. 2A, the user has selected the icon representing the "GI symptoms" complaint in sub-region 206a, and region 204a of screen 200a is accordingly displaying sub-regions 208a-224a which pertain to the GI symptoms complaint.

In some embodiments, symptoms sub-region 208a may be configured to allow a user to indicate information regarding one or more symptoms for a patient. In some embodiments, the symptoms indicated may be associated by the system with a respective complaint under which the user is working.

As shown in FIG. 2A, symptoms sub-region 208a comprises a plurality of icons/buttons that may be selected and/or deselected by a user of GUI 200, for example by tapping or clicking the icons/buttons. In some embodiments, a user may tap or click the icon/button in order to toggle it between not selected and selected; between not selected and deselected; between selected and deselected; or between not selected, selected, and deselected. In some embodiments, not selecting an option may indicate an absence of information associated with the option (e.g., the symptom is not reported as being present nor as being absent), selecting an option may affirm the information associated with the option (e.g., the symptom is reported as present), and deselecting an option may expressly disaffirm the information associated with the option (e.g., the symptom is expressly reported as being not present). In some embodiments, a button/icon may toggle between different appearances, shadings, and/or colors to indicate whether the button/icon is not selected (e.g., gray), selected (e.g., green), or deselected (e.g., red).

In some embodiments, GUI 200 may be configured to require a user to make a selection or deselection of any one or more options within an option group (e.g., a group of options displayed in a sub-region, or a subgroup of options displayed within a sub-region). In some embodiments, GUI 200 may be configured to require a user to make a selection or deselection of a specific option (e.g., the user may be disallowed from leaving the option neither selected nor deselected). In some embodiments, a user may be able to leave one or more (or all) options in a group neither selected nor deselected. (In some embodiments, a sub-region may include a single option group; in some embodiments, sub-region may include multiple separate option groups.)

In some embodiments, a user may not be permitted to select more than predetermined maximum number of options in an option group, wherein the predetermined maximum number of options may be as low as 1 (or in some embodiments may be as low as 0, e.g., if one or more other selections made by the user in a different sub-region of GUI 200 logically preclude selection of any of the options in the group). In some embodiments, a user may permitted to select any number of options in an option group. In some embodiments, a user may be required to select a number of options in an option group within a predetermined range. In some embodiments, a user may be required to select exactly a predetermined number of options in an option group.

In the example of sub-region 208a in FIG. 2A, sub-region 208a includes eight option buttons each representing a potential symptom. As shown, the user has selected two of the options—"nausea" and "hematochezia"—and left the other six options not selected. Accordingly, the system has generated a natural-language statement regarding the two selected symptom options and displayed said statement in the canvas region of screen 200a: "The patient's symptoms include nausea and hematochezia."

In addition to the selectable option buttons/icons, sub-region 208a also includes a free text field into which a user may manually type a statement or other text. In some embodiments, text typed into the free text field may be inserted directly into the natural-language entry being generated and displayed on canvas portion 202a. In some embodiments, text typed into the free text field of a sub-region may be displayed immediately after (or immediately before) any automatically-generated text created on the basis of the options that are (or are not) selected or deselected in the option group. Thus, in the example of sub-region 208a, text entered into the free text field may be displayed in canvas region 202a after the sentence "The patient's symptoms include nausea and hematochezia." The grammatical structure of the natural language statement(s) generated and displayed in canvas portion 202a, including the manner in which said statement(s) incorporate(s) one or more options that are selected or deselected in menu region 204a, may be determined by the system (e.g., engine 102) in accordance with a template being applied to the patient consultation.

The other sub-regions 209a-224a shown in FIG. 2 may include similar sets of selectable and/or deselectable options, may include similar free-text fields, and may be configured to allow a user to generate a natural-language statement based on selection and/or deselection of options in a similar manner as described above with reference to sub-region 206a.

In some embodiments, onset sub-region 209a may be configured to allow a user to indicate information regarding symptom onset for a patient. In some embodiments, the symptom onset information may be associated by the system with a respective complaint under which the user is working.

In some embodiments, timing sub-region 210a may be configured to allow a user to indicate information regarding symptom timing for a patient. In some embodiments, the symptom timing information may be associated by the system with a respective complaint under which the user is working. As shown, timing sub-region 210a includes a free-text field as well as seven option buttons each representing a potential symptom timing descriptor. As shown, the user has selected one of the options—"during the day"—and left the other six options not selected. Accordingly, the system has generated a natural-language statement regarding the selected symptom timing option and displayed said statement in the canvas region of screen 200a: "The symptoms occur during the day."

In some embodiments, frequency sub-region 212a may be configured to allow a user to indicate information regarding symptom frequency or the frequency of any other medically-relevant occurrence (e.g., frequency of bowel movements) for a patient. In some embodiments, the frequency information may be associated by the system with a respective complaint under which the user is working. As shown, frequency sub-region 212a includes a free-text field as well as four option buttons each representing a potential frequency descriptor. As shown, the user has selected one of the options—"frequently"—and left the other three options not selected. Accordingly, the system has generated a natural-language statement regarding the selected frequency option and displayed said statement in the canvas region of screen 200a: "She has bowel movements frequently."

In some embodiments, location sub-region 214a may be configured to allow a user to indicate information regarding symptom location for a patient. In some embodiments, the symptom location information may be associated by the system with a respective complaint under which the user is working. As shown, location sub-region 214a includes a free-text field as well as seven option buttons each representing a potential frequency descriptor. As shown, the user has selected one of the options—"LUQ"—and left the other six options not selected. Accordingly, the system has generated a natural-language statement regarding the selected location option and displayed said statement in the canvas region of screen 200a: "Location includes LUQ."

In some embodiments, context sub-region 216a may be configured to allow a user to indicate information regarding contextual information for a patient. In some embodiments, the contextual information may be associated by the system with a respective complaint under which the user is working. As shown, context sub-region 216a includes a free-text field as well as six option buttons each representing a potential frequency descriptor. As shown, the user has not selected any of the option buttons in context sub-region 216a, and there is accordingly no natural-language statement regarding context options generated and displayed in the canvas region of screen 200a.

In some embodiments, quality sub-region 218a may be configured to allow a user to indicate information regarding symptom quality for a patient. For example, a symptom quality may be a descriptor that characterizes a quality of a symptom, such as "stabbing" pain, "dull" pain, or "throbbing" pain. In some embodiments, the symptom quality information may be associated by the system with a respective complaint under which the user is working.

In some embodiments, severity sub-region 220a may be configured to allow a user to indicate information regarding symptom severity for a patient. For example, a symptom severity may be a descriptor that characterizes a severity of a symptom, such as "intense" pain, "moderate" pain, or "mild" pain. In some embodiments, the symptom severity information may be associated by the system with a respective complaint under which the user is working.

In some embodiments, sick contacts sub-region 222a may be configured to allow a user to indicate information regarding contacts for a patient. In some embodiments, a contact may indicate a person, place, or activity with which the patient has been in contact. In some embodiments, the contacts information may be associated by the system with a respective complaint under which the user is working.

In some embodiments, aggravating factors sub-region 224a may be configured to allow a user to indicate information regarding aggravating factors for a patient. In some embodiments, the aggravating factor information may be associated by the system with a respective complaint under which the user is working.

As shown by the natural-language statements displayed in canvas region 202a, the system (e.g., system 100) has generated various natural-language statements in accordance with options selected (e.g., buttons selected) by the user in menu region 204a of GUI 200. In some embodiments, one statement may be generated and displayed per option selected. In some embodiments, multiple selected options may be included in a single statement (e.g., by being listed in series with one another). In some embodiments, one or more option from different option groups—e.g., from different sub-regions of menu region 204a and pertaining to different types of information—may be included in a single natural-language sentence together with one another; for example, a generated sentence may describe both a symptom identity and its timing (e.g., "The patient reports frequent nausea.").

In some embodiments, canvas region 202a may display different natural-language statements separately from one another (e.g., by displaying them on different lines from one another). For example, a natural language-statement generated in accordance with inputs executed via a first sub-region of menu region 204a may be displayed on a separate line from a natural-language statement executed via a second sub-region of menu region 204a. In this way, a user of GUI 200 may be able to easily view changes as they are dynamically made to different natural-language statements in canvas region 202a as the user selects and/or deselects different options in menu region 204a.

In some embodiments, canvas region 202a may display one or more of the generated natural-language statements in a predefined paragraph structure, section structure, and/or document structure. For example, as shown in FIG. 2A, the sentences generated and displayed in region 202a are displayed under two separate headings (the headings shown in bold) with one sentence under the first heading and four sentences under the second heading. The arrangement of one or more sentences into different paragraphs, sections, headings, etc. in canvas region 202a may be defined by system 200 in accordance with a template being applied to generation of the natural-language entry for storage in an electronic health record.

In some embodiments, the arrangement of one or more generated statements into different paragraphs, sections, headings, etc. in canvas region 202a may be the same or different from the arrangement of the same generated statements in a review format and/or output format generated by the system and used for storage of the natural-language statements in an electronic health record. For example, canvas region 202a may display one or more statements on individual lines for easy viewing and editing during a note creation process, whereas the system may then collapse one or more of those sentences into a single line or into a single paragraph upon approval of the sentences by the user, such that the sentences are saved in a unified paragraph form in the electronic health record.

In addition to canvas region 202a and menu region 204a, screen 200a of GUI 200 further includes patient visit selection region 226a. In some embodiments, region 226a may be configured to allow a user of GUI 200 to select a patient visit under which a natural-language entry for a medical record (e.g., a note) should be created. In some embodiments, a user may first specify a patient visit and then specify information about patient demographics, patient complaint, and all other medical information in menu region 204a afterwards, such that all specified information may be associated with the indicated patient visit. In some embodiments, there may be a one-to-one relationship between a patient visit and a note (or other natural-language entry for storage in a medical record) generated by the system, such that the system may be configured to create and store one note per patient visit.

In some embodiments, region 226a may be configured to display patients and/or patient visits in list form, such that a user may click or tap to select a patient and/or patient visit. In some embodiments, options for selecting a patient visit may be nested under options for selecting a patient, such that different visit options may be displayed as items under a patient dropdown option. In some embodiments, one or more GUI objects (e.g., selectable icons) may be displayed for allowing a user to add a new patient and/or a new visit.

Selecting a patient visit and/or adding a new patient visit may, in some embodiments, automatically cause display of a canvas region and menu region for building a note for the selected and/or newly-added visit.

In some embodiments, selecting and/or adding a new patient visit may cause the system to automatically import patient demographic information (e.g., into a menu region, as discussed below with respect to FIG. 2B) based on demographic information entered for the patient during creation of another note pertaining to another visit.

Figure 2B:
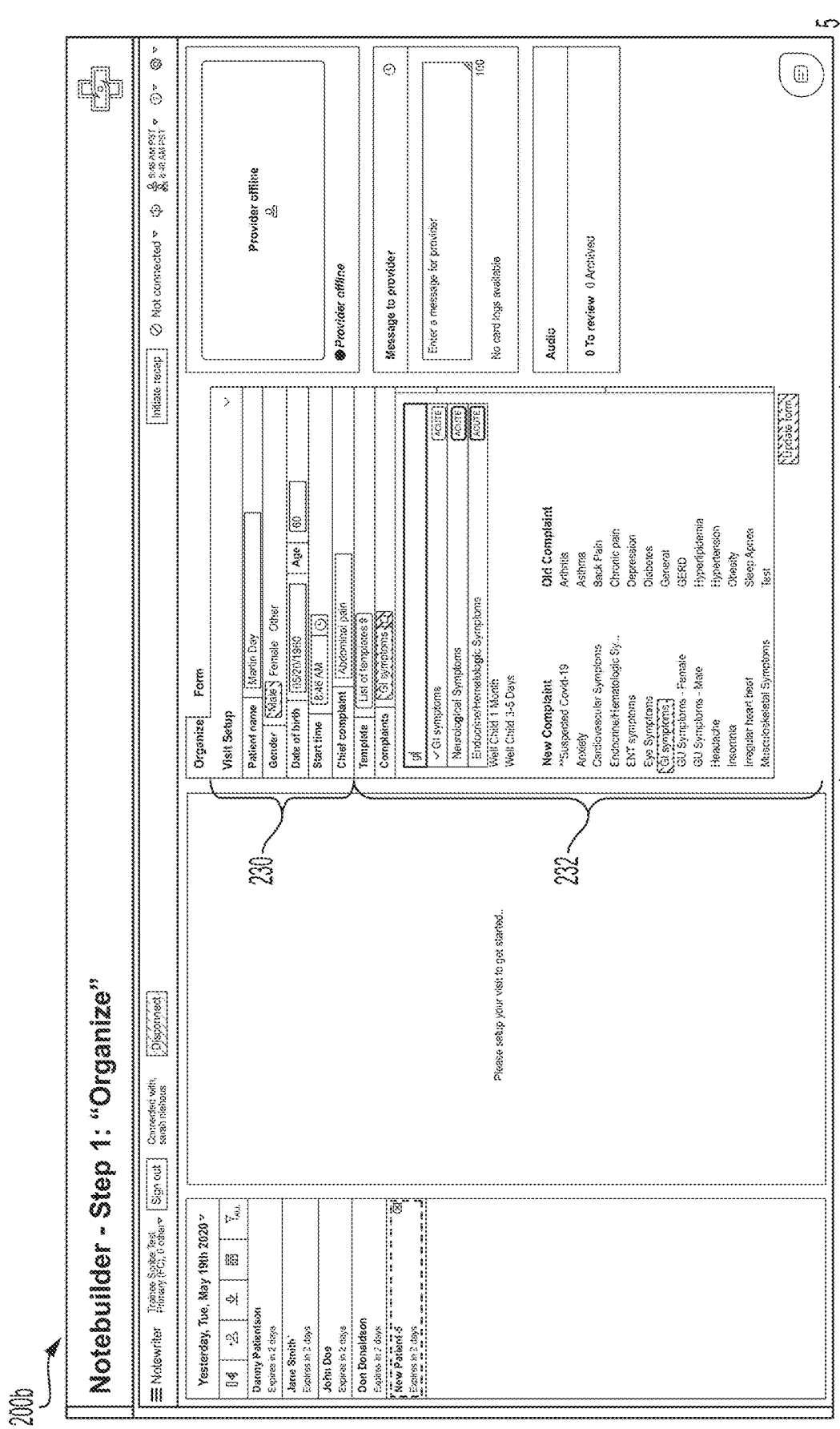

FIG. 2B depicts screen 200b of a graphical user interface 200, in accordance with some embodiments. Screen 200b depicts GUI 200 during the process of organizing or setting up the interface for capture of information during a patient visit. As shown in FIG. 2B, no canvas region is displayed during the setup process, and instead the user is prompted to specify patient demographic information and patient complaint information in menu region 204b before the canvas region is displayed. The description of screen 200b below provides an overview of certain functionalities of the systems and platforms disclosed herein, with aspects of screen 200b that are the same or similar as screen 200a not described or described only briefly, and with corresponding reference numerals used for same/similar portions of the screens (e.g., menu region 204b may share one or more features in common with menu region 204a).

As shown in FIG. 2B, menu region 204b of screen 200b displays options for an "organize" step of the note-building process, as opposed to the options for the "capture" step of the note-building process described above with reference to screen 200a in FIG. 2A. In some embodiments, an "organize" step may refer to the step of capturing patient demographic information, patient consultation metadata, and/or the identity of one or more patient complaints to be used to determine which template should be selected by the system and used to provide GUI screens for capturing patient medical information regarding the patient's symptoms and other medical information relevant to the specified complaints. In some embodiments, a user of GUI 200 may select one or more complaints at the "organize" step before the system provides one or more GUI screens for inputting symptom information and other information relevant to the complaint during the patient consultation.

As shown in FIG. 2B, menu region 204b may include demographic information region 230 and complaint selection region 232.

Demographic region 204b may be a GUI region configured to accept inputs from a user regarding patient demographic information including but not limited to name, gender, and date of birth. Demographic region 204b may be further configured to accept inputs from a user regarding consultation metadata, such as consultation time and/or location. In some embodiments, demographic information indicated via a demographic region of a GUI may be used by the system to filter available complaints, to configure a template for collecting symptom information and/or medical information at a capture stage, and/or to configure natural-language phrases generated by the system using appropriate pronouns.

Complaint selection region 232 may be a GUI region configured to accept inputs from a user regarding one or more complaints to be associated with the patient consultation. In some embodiments, complaint selection region 232 may include a text field into which a user may type a chief complaint. In some embodiments, complaint selection region 232 may include a search field into which a user may type text to search for one or more complaints to be added to associated with the consultation; in some embodiments, the complaint template used by the system to generate and/or provide the user interface screens for capturing patient symptom and medical information may be generated, selected, and/or configured in accordance with the one or more complaints indicated by the user via complaint selection region 232.

In some embodiments, a complaints selection region may be configured to allow a user to specify one or more complaints via typing into a text field, selecting from a drop down menu, and/or selecting from a list of displayed options. In some embodiments, as a user types into a search field, suggested complaints to be added to the template may be automatically displayed to the user. In some embodiments, suggested complaints may be organized into a group of "new complaints" and a group of "old complaints" according to records accessible by the system regarding what complaints the same patient has previously presented with. In some embodiments, the displayed suggested complaints may be selectable user interface icons that can be clicked or tapped by a user in order to be added to the template being configured for the patient consultation. In some embodiments, the suggested complaints that are displayed to the user may be filtered, automatically and/or in accordance with user input, in accordance with clinician specialty, medical facility, country region, state, patient identity, patient demographic information, and/or reason for patient visit.

As shown in the example of FIG. 2B, the user has clicked on "GI Symptoms" under the heading "New Complaint", and a "GI Symptoms" complaint has been added to the template being configured, such that prompts for information regarding GI Symptoms will subsequently be displayed to the user at the capture stage.

Figure 2C:
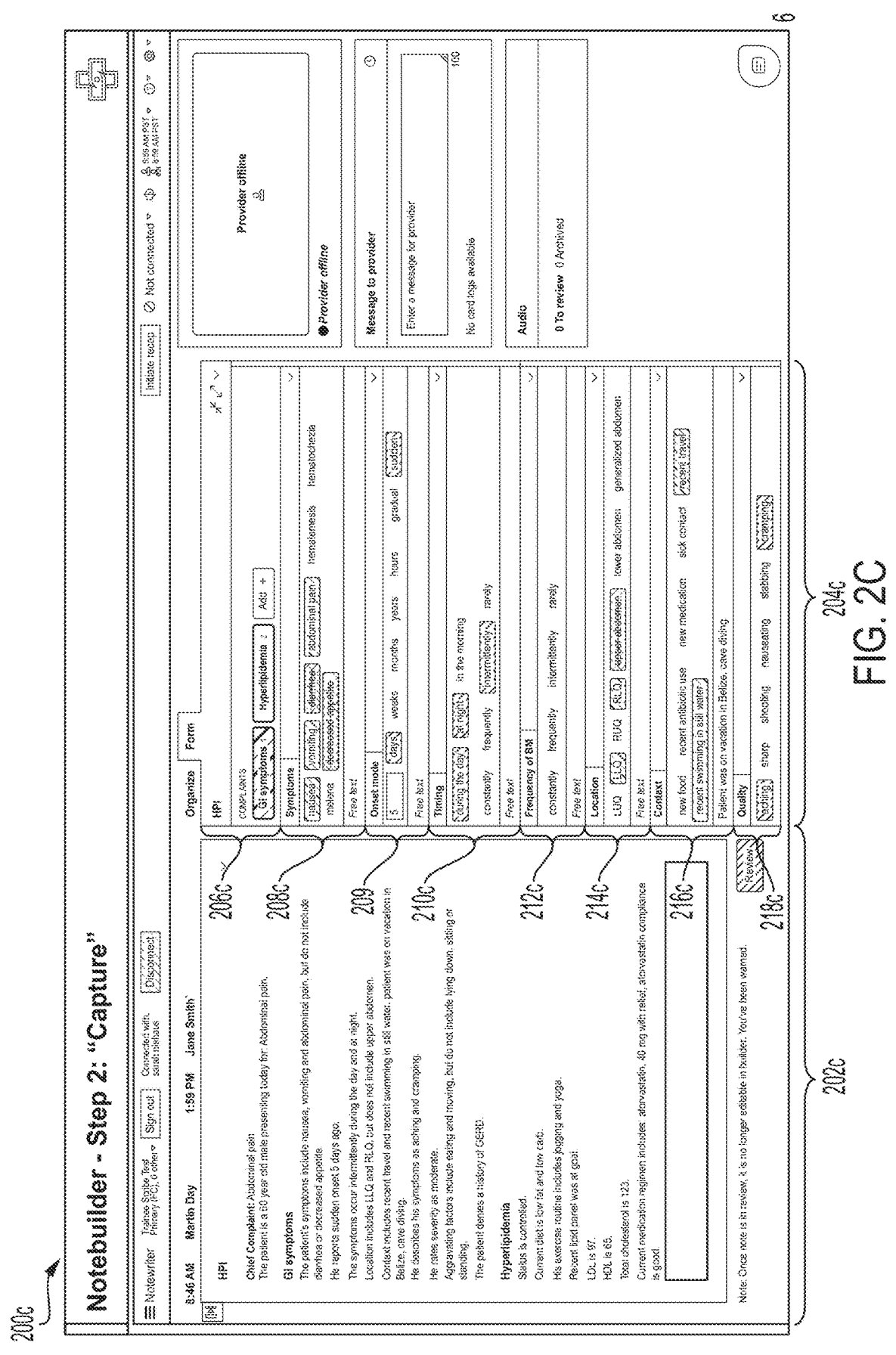

FIG. 2C depicts screen 200c of a graphical user interface 200, in accordance with some embodiments. Screen 200c depicts GUI 200 during the process of capturing of information during a patient visit (e.g., following a set-up/organize stage). As shown in FIG. 2C, a canvas region 202c and a menu region 204c are displayed during the capture process. The description of screen 200c below provides an overview of certain functionalities of the systems and platforms disclosed herein, with aspects of screen 200c that are the same or similar as screen 200a not described or described only briefly, and with corresponding reference numerals used for same/similar portions of the screens (e.g., menu region 204c may share one or more features in common with menu region 204a).

In some embodiments, canvas region 202c may share any one or more features in common with canvas region 202a described above with reference to FIG. 2A; similarly, menu region 204c may share any one or more features in common with menu region 204a described above with reference to FIG. 2A.

In the example of screen 200c in FIG. 2C, screen 200c may be configured to capture information (e.g., symptom information and/or other medical information) related to two complaints: "GI Symptoms" and "Hyperlipidemia," each of which are shown in complaints sub-region 206c. These two complaints may have been indicated by a user at a set-up phase, e.g., using screen 200b. As shown in complaints sub-region 206c, the "GI Symptoms" complaint has been selected by a user (and is accordingly highlighted by being shown in bold); accordingly, the other sub-regions shown in menu region 204c may be sub-regions corresponding to symptom information and other medical information relevant to the "GI Symptoms" complaint. If the user tapped or clicked on the "Hyperlipidemia" complaint button/icon in sub-region 206c, then GUI 200 may replace display of the "GI Symptoms" sub-regions shown in screen 200c with a different set of sub-regions relevant to the hyperlipidemia complaint.

In the example of FIG. 2C, other sub-regions included in menu region 204c may include symptoms sub-region symptoms sub-region 208c, onset mode sub-region 209c, timing sub-region 210c, frequency sub-region 212c, location sub-region 214c, context sub-region 216c, and quality sub-region 218c. The sub-regions 208c-218c may chare one or more features in common with respective sub-regions 208a-218a as described above with reference to screen 200a in FIG. 2A.

In some embodiments, symptoms sub-region 208c may be configured to allow a user to indicate information regarding symptom onset for a patient. In some embodiments, the symptom onset information may be associated by the system with a respective complaint under which the user is working (e.g., "GI symptoms"). As shown, symptoms sub-region 208c includes a free-text field as well as eight option buttons each representing a potential symptom descriptor. As shown, the user has selected three of the options, "nausea," "vomiting," and "abdominal pain"; has deselected two of the options, "diarrhea" and "decreased appetite"; and has left the other three options not selected. Accordingly, the system has generated a natural-language statement regarding the selected and deselected symptom options and displayed said statement in canvas region 202c: "The patient's symptoms include nausea, vomiting, and abdominal pain, but do not include diarrhea or decreased appetite."

In some embodiments, onset sub-region 209c may be configured to allow a user to indicate information regarding symptom onset (e.g., onset mode and/or onset timing) for a patient. In some embodiments, the symptom onset information may be associated by the system with a respective complaint under which the user is working. As shown, onset sub-region 209c includes a free-text field as well as a number-entry field and seven option buttons arranged into two option groups. The option group on the right pertains to onset mode, and the user has selected the option indicating a "sudden" onset mode and left the option indicating a "gradual" onset mode not selected. The option group on the left pertains to onset timing and includes five option buttons and an associated number entry field. As shown, the user has selected the option indicating a number of "days" and has left the other four options not selected; the user has entered t number "5" into the number entry field, thereby specifying an onset timing of five days. In accordance with the options selected and information entered in both option groups, the system has generated a natural-language statement and displayed said statement in canvas region 202c: "He reports sudden onset five days ago."

In some embodiments, timing sub-region 210c may be configured to allow a user to indicate information regarding symptom timing for a patient. In some embodiments, the symptom timing information may be associated by the system with a respective complaint under which the user is working. As shown, timing sub-region 210c includes a free-text field as well as seven option buttons each representing a potential symptom timing descriptor. As shown, the user has selected three of the options—"during the day," "at night," and "intermittently"—and left the other four options not selected. Accordingly, the system has generated a natural-language statement regarding the selected symptom timing option and displayed said statement in canvas region 202c: "The symptoms occur intermittently during the day and at night."

In some embodiments, frequency sub-region 212c may be configured to allow a user to indicate information regarding symptom frequency or the frequency of any other medically-relevant occurrence (e.g., frequency of bowel movements) for a patient. In some embodiments, the frequency information may be associated by the system with a respective complaint under which the user is working. As shown, frequency sub-region 212c includes a free-text field as well as four option buttons each representing a potential frequency descriptor. As shown, the user has left all four options not selected. Accordingly, the system has not generated/displayed a sentence regarding frequency in canvas region 202c.

In some embodiments, location sub-region 214c may be configured to allow a user to indicate information regarding symptom location for a patient. In some embodiments, the symptom location information may be associated by the system with a respective complaint under which the user is working. As shown, location sub-region 214c includes a free-text field as well as seven option buttons each representing a potential frequency descriptor. As shown, the user has selected two of the options, "LLQ" and "RLQ"; deselected one of the options, "upper abdomen"; and left the other four options not selected. Accordingly, the system has generated a natural-language statement regarding the selected and deselected location options and displayed said statement in canvas region 202c: "Location includes LLQ and RLQ, but does not include upper abdomen."

In some embodiments, context sub-region 216c may be configured to allow a user to indicate information regarding contextual information for a patient. In some embodiments, the contextual information may be associated by the system with a respective complaint under which the user is working. As shown, context sub-region 216c includes a free-text field as well as six option buttons each representing a potential frequency descriptor. As shown, the user has selected two of the option buttons—"recent travel" and "recent swimming in still water"—and left the other four options not selected. Accordingly, the system has generated a natural-language statement regarding the selected context options and displayed said statement in canvas region 202c: "Context includes recent travel and recent swimming in still water." Furthermore, the user has typed a sentence into the free text field in sub-region 216c, and the sentence has been appended onto the end of the natural-language statement generated in accordance with the selected input options and displayed in canvas region 202c.

In some embodiments, quality sub-region 218c may be configured to allow a user to indicate information regarding symptom quality for a patient. In some embodiments, the symptom quality information may be associated by the system with a respective complaint under which the user is working. As shown, quality sub-region 218c includes a free-text field as well as six option buttons each representing a potential symptom quality descriptor. As shown, the user has selected two of the option buttons—"aching" and "cramping"—and left the other four options not selected. Accordingly, the system has generated a natural-language statement regarding the selected symptom quality options and displayed said statement in canvas region 202c: "He describes his symptoms as aching and cramping."

In some embodiments, a menu region such as menu region 204c may be configured such that one or more sub-regions, option groups, and/or options may be displayed or suppressed from display in accordance with one or more options selected in the menu region by the user. For example, the system may be configured to automatically display certain options regarding symptoms, symptom characteristics, tests, and/or medication in accordance with symptom information and/or other medical information indicated by the user via selection of one or more options. In some embodiments, the system may be configured to prioritize or deprioritize (e.g., by displaying in a higher position in a list) one or more sub-regions, option groups, and/or options in accordance with one or more options selected in the menu region by the user.

As shown on canvas region 202c, a canvas region may display automatically-generated natural-language statements organized into different sections in accordance with the template being applied. In some embodiments, when a user has indicated more than one complaint for a patient consultation, a canvas region may display separate sections for statements pertaining to the different complaints. In the example of screen 200c, canvas region 202c includes a first section including statements pertaining to the "GI symptoms" complaint and a second section including statements pertaining to the "hyperlipidemia" complaint.

In some embodiments, a user of GUI 200 may be able to edit automatically-generated statements and/or statements generated based on text typed into free-text fields by typing/editing directly on a canvas region such as canvas region 202c.

In some embodiments, GUI 200 may be configured such that, alternatively or additionally to natural-language statements being automatically displayed in canvas region 202c, natural-language statements may be automatically suggested for display in canvas region 202c. For example, the system may suggest a sentence (e.g., by displaying the suggested sentence in another region of the screen or by displaying it in a provisional format such as grayed-out text) that the user may approve for display (or non-provisional display) in canvas region 202c.

FIG. 2D depicts a screen 200d of a graphical user interface of a natural-language medical record generation platform, in accordance with some embodiments. Screen 200d depicts GUI 200 during the process of reviewing a plurality of natural-language statements generated during a capture stage; after capture, a user may execute one or more inputs to cause GUI 200 to enter a review mode such as the review mode shown by screen 200d. As shown in FIG. 2D, instead of including a canvas portion and a menu portion, screen 200d includes review portion 240.

In some embodiments, a review portion such as review portion 240 may be configured to display the natural-language statements generated based on the inputs received during the capture stage, wherein the statements are displayed on the review portion in a review format. In some embodiments, a review portion may display one or more statements in paragraph form rather than on individual lines, such that the sentences are saved in a unified paragraph form in the electronic health record. In some embodiments, a user of GUI 200 may be able to specify by one or more user-adjustable settings whether or not statements are collapsed from separate lines into paragraph format at the review stage.

In some embodiments, screen 200d may be configured to allow a user to edit one or more of the generated natural-language statements at the review stage, for example by allowing a user to manually execute word-processing inputs into review portion 240 in order to add text, delete text, or modify text displayed in review portion 240. In some embodiments, screen 200d may enable a user to apply one or more automated editing or review tools such as spell-check.

Figure 3:
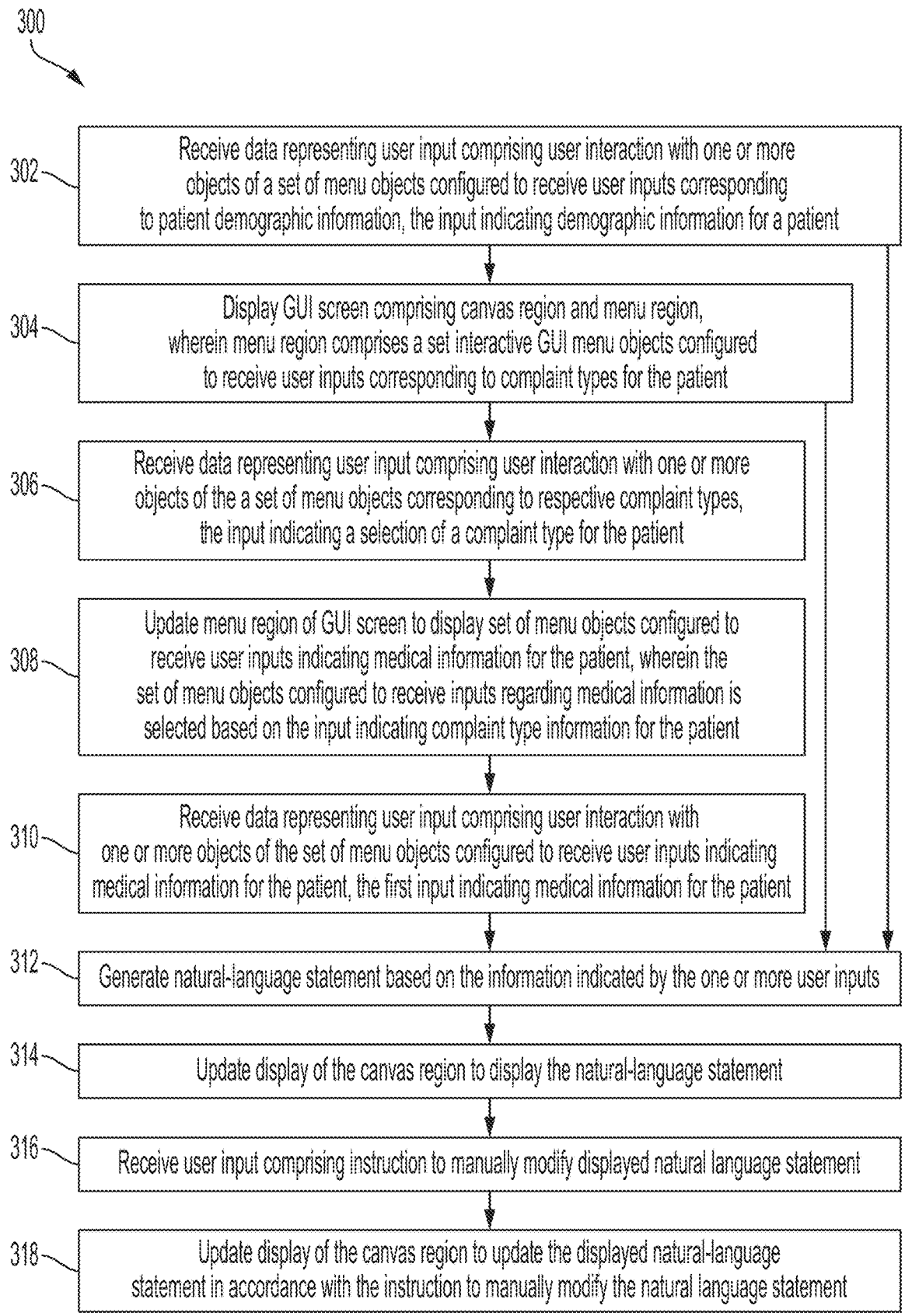
FIG. 3 depicts a flow chart describing a method for providing a natural-language medical record generation platform, in accordance with some embodiments.

FIG. 3 depicts a flow chart describing method 300 for providing a natural-language medical record generation platform, in accordance with some embodiments. In some embodiments, method 300 may be performed by a system for providing a natural-language medical record generation platform, such as system 100 described above with reference to FIG. 1. As described below, method 300 may include providing one or more GUI screens for accepting user inputs regarding patient demographic information, patient complaint information, and/or patient medical information and for displaying and/or editing one or more natural-language statements generated based on the received user inputs. In some embodiments, the one or more GUI screens displayed in method 300 may include (or may share one or more features in common with) one or more of GUI screens 200a-200D described above in FIGS. 2A-2D.

At block 302, in some embodiments, the system may receive data representing a user input comprising a user interaction with one or more objects of a set of objects configured to receive user inputs corresponding to patient demographic information, the user input indicating demographic information for a patient. The system may receive any data representing a user input comprising an indication of patient demographic information. In some embodiments, a user may execute an input indicating patient demographic information by interacting with one or more GUI objects (e.g., text fields, drop-down menus, check-boxes, selectable and/or deselectable buttons/icons).

In some embodiments, the receipt of inputs indicating patient demographic information at block 302 may include receiving inputs executed by a user via a user interface screen configured to accept inputs regarding patient demographic information, such as GUI screen 200b described above with respect to FIG. 2B. For example, a user may indicate patient demographic information by inputting information into demographic information region 230 of GUI screen 200b; a user may type information such as a patient name into a text field, may indicate information such as patient date of birth by using a drop-down menu, and/or may indicate patient gender by selecting one or more selectable icons.

In some embodiments, the system may be configured to determine which menu options to display to a user based on the indicated demographic information, such as by configuring a template such that GUI options available to the user are selected and presented based on patient age, gender, or other demographic information. Furthermore, as explained further below, the system may configure the structure of one or more natural-language statements based on the indicated demographic information, such as by inserting the patient's name into the statement and/or by configuring pronouns in the statement according to the indicated gender for the patient.

At block 304, in some embodiments, the system may display a GUI screen comprising a canvas region and a menu region, wherein the menu region comprises a set of interactive GUI menu objects configured to receive user inputs corresponding to complaint types for the patient. In some embodiments, the displayed GUI screen may be (or may share one or more features in common with) GUI screen 200c including canvas region 202c and menu region 204c, as described above with respect to FIG. 2C. The set of interactive GUI menu objects configured to receive user inputs corresponding to complaint types may include (or may share one or more features in common with) the selectable/deselectable icons indicating patient complaints in complaints sub-region 206c. In accordance with a user selecting, adding, or removing a complaint type by interacting with one or more of the icons in complaints sub-region 206c (and/or in accordance with a user otherwise indicating one or more complaints via interaction with the GUI), the system may responsively cause display of one or more GUI objects configured to receive inputs regarding medical information pertinent to an indicated complaint.

At block 306, in some embodiments, the system may receive data representing user input comprising user interaction with one or more objects of the set of menu objects corresponding to respective complaint types, the input indicating a selection of a complaint type for the patient. In the example of FIG. 2C, the user has selected the icon for the "GI Symptoms" complaint, as indicated by the fact that the "GI Symptoms" icon is shown in bold typeface.

At block 308, in some embodiments, the system may update the menu region of the GUI screen to display a set of menu objects configured to receive user inputs indicating medical information for the patient, wherein the set of menu objects configured to receive inputs regarding medical information is selected based on the input indicating complaint type for the patient. The system may select the menu objects that are displayed by selecting from among a plurality of predetermined sets of one or more menu objects, each of the plurality of sets of one or more menu objects corresponding to a different respective complaint. In some embodiments, the system may select which menu objects are displayed based on known patient information, demographic information, practitioner information, and/or a user indication of a specialty, a healthcare system, a payer, and/or a clinician.

In some embodiments, the system may display one or more GUI objects and/or GUI regions configured to accept inputs regarding patient medical informant pertinent to an indicated complaint. In some embodiments, the indicated complaint may be indicated by selection of one or more GUI objects configured to receive inputs regarding complaint types as described above.

In some embodiments, the set of menu objects configured to receive inputs regarding medical information may include one or more text fields, drop-down menus, check-boxes, selectable and/or deselectable buttons/icons. In some embodiments, the system may display GUI objects for accepting inputs regarding medical information organized into groups of GUI objects, such as the selectable/deselectable icons organized into various sub-regions and/or into one or more separate object groups therein, as shown in the example of FIG. 2C.

In the example of FIG. 2C, the user has selected the icon for the "GI Symptoms" complaint in complaints sub-region 206c, and the system has accordingly displayed sub-regions 208c-218c each including one or more GUI objects configured to accept user inputs regarding medical information pertinent to the "GI Symptoms" complaint. The system may automatically determine which sub-regions, which GUI objects therein, and/or which GUI object groups therein are to be displayed to the user based at least in part on a complaint indicated by the user.

In some embodiments, the sub-regions, GUI objects, and/or GUI object groups configured to accept inputs regarding patient medical information may further be automatically determined and selected by the system on the basis of indicated patient demographic information (e.g., information indicated at block 302 and/or via a demographic information GUI region such as demographic information region 230 of GUI screen 200b. In some embodiments, the sub-regions, GUI objects, and/or GUI object groups configured to accept inputs regarding patient medical information may further be automatically determined and selected by the system on the basis of previously-indicated medical information for the patient, such that one or more indications of medical information (e.g., inputs made by the user to menu region 204c via one or more of sub-regions 208c-218c) may cause the system to automatically and dynamically update the displayed GUI objects for indicating medical information. For example, if a user makes an indication of medical information that the system determines may exclude the possibility of another line of inquiry being relevant, then options pertaining to that line of inquiry may be automatically suppressed from display by the system.

In some embodiments, the displayed menu objects may be arranged into one or more subsets, such as subsets relating to respective potential symptoms, respective potential symptom onset characterizations, respective potential symptom timing information, respective potential symptom frequency, respective potential symptom locations, respective potential contextual information, respective potential symptom quality, respective potential prior medical conditions, respective potential diagnoses, represents a respective potential current medications, respective potential medications to be prescribed, respective potential current treatments, and/or respective potential treatment to be prescribed.

At block 310, in some embodiments, the system may receive data representing a user input comprising a user interaction with one or more objects of the set of menu objects configured to receive user inputs indicating medical information for the patient, the first input indicating medical information for the patient. For example, as described above with reference to FIG. 2C, a user of the system may enter text into one or more fields, select one or more drop-down menu items, and/or select or deselect one or more selectable/deselectable icons/buttons.

At block 312, in some embodiments, the system may generate a natural-language statement based on the information indicated by the one or more user inputs. In some embodiments, the natural-language statement generated may be generated based on a natural-language statement structure indicated by one or more templates applied by the system based on indicated patient demographic information (e.g., as indicated at block 302), indicated complaint information (e.g., as indicated at block 306), and/or indicated patient medical information (e.g., as indicated at block 312). In some embodiments, generating the natural-language statement based on the medical information indicated by the first user input comprises inserting a text string associated with the indicated medical information into a predefined syntactical structure. In some embodiments, the natural-language statement may be generated based on multiple user inputs indicating multiple aspects of patient demographic and/or medical information.

In some embodiments, in addition to or alternately to a natural-language statement being generated by the system based on one or more selections of options by a user, a natural language statement may be generated by the system based in whole or in part on text entered by a user into a text field. For example, the system may insert a character string entered into a text field by a user into a predetermined natural-language sentence structure. In some embodiments, the system may insert a character string entered into a text field by a user into a predetermined natural-language paragraph structure as a complete sentence.

At block 314, in some embodiments, the system may update display of the canvas region to display the natural-language statement. As show in the example of FIG. 2C, various natural-language statements based on user inputs made in menu region 204*c* are displayed in canvas region 202*c*.

At block 316, in some embodiments, the system may receive a user input comprising an instruction to manually modify the displayed natural-language statement. At block 318, in some embodiments, the system may update display of the canvas region to update the displayed natural-language statement in accordance with the instruction to manually modify the natural-language statement.

In some embodiments, an instruction to manually modify one or more automatically-generated natural language statements displayed on a canvas region may be made by a user directly via a canvas region of a GUI or via another region/portion/object of a GUI including the canvas region. For example, in some embodiments, a user may be permitted to type directly into a canvas region to add to, delete from, or modify portions of an automatically-generated natural language statement displayed therein.

In some embodiments, a user may be permitted to manually modify a natural-language statement displayed at a review screen of a GUI, distinct from a canvas region, such as review portion 240 of screen 200*d* described above with respect to FIG. 2D. In some embodiments, functionality for manually revising a natural-language statement at a review screen may be provided additionally or alternatively to functionality for revising a natural-language statement directly in a canvas portion such as portion 202*c* of screen 200*c*.

Figure 4A:
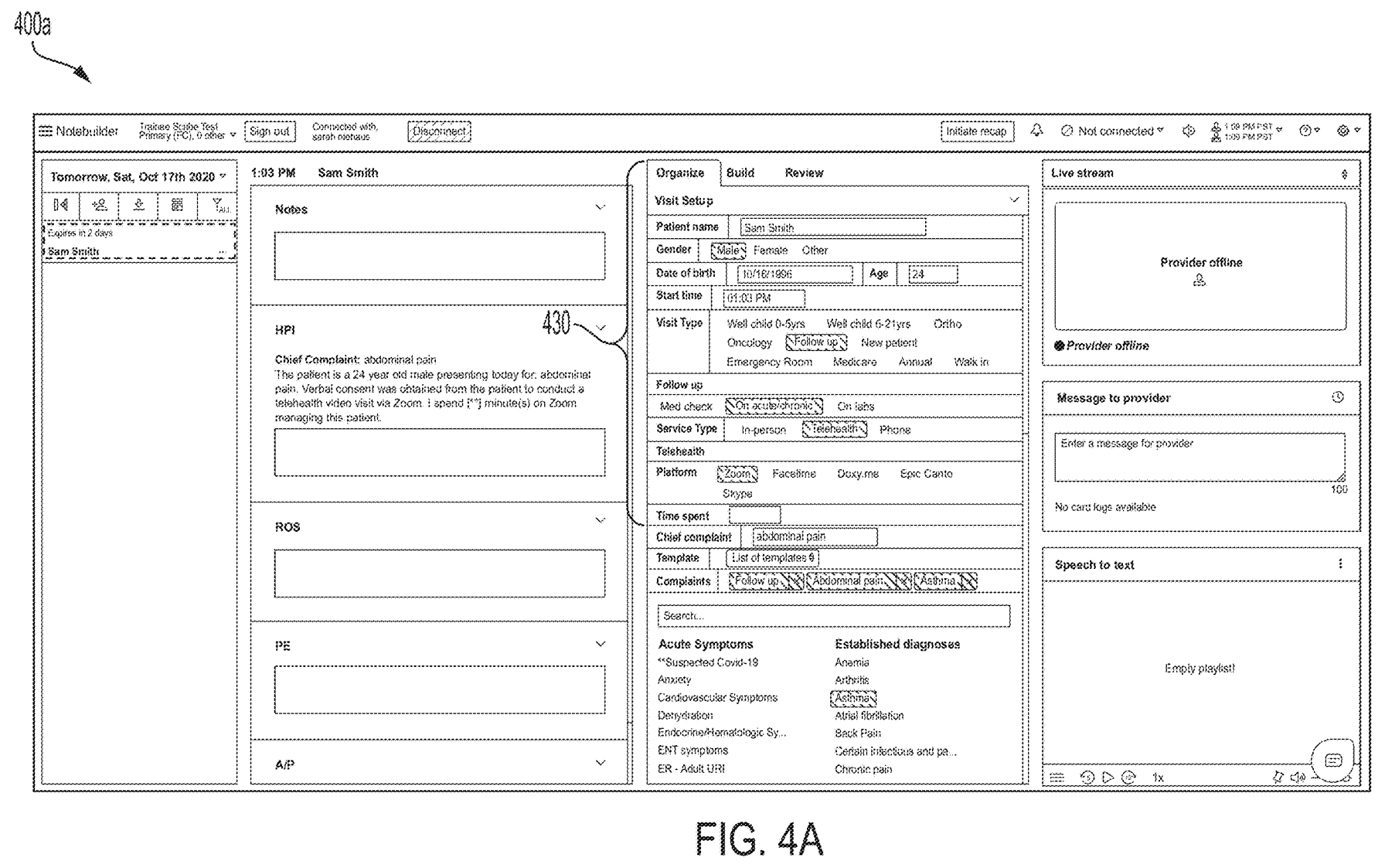
Figure 4B:
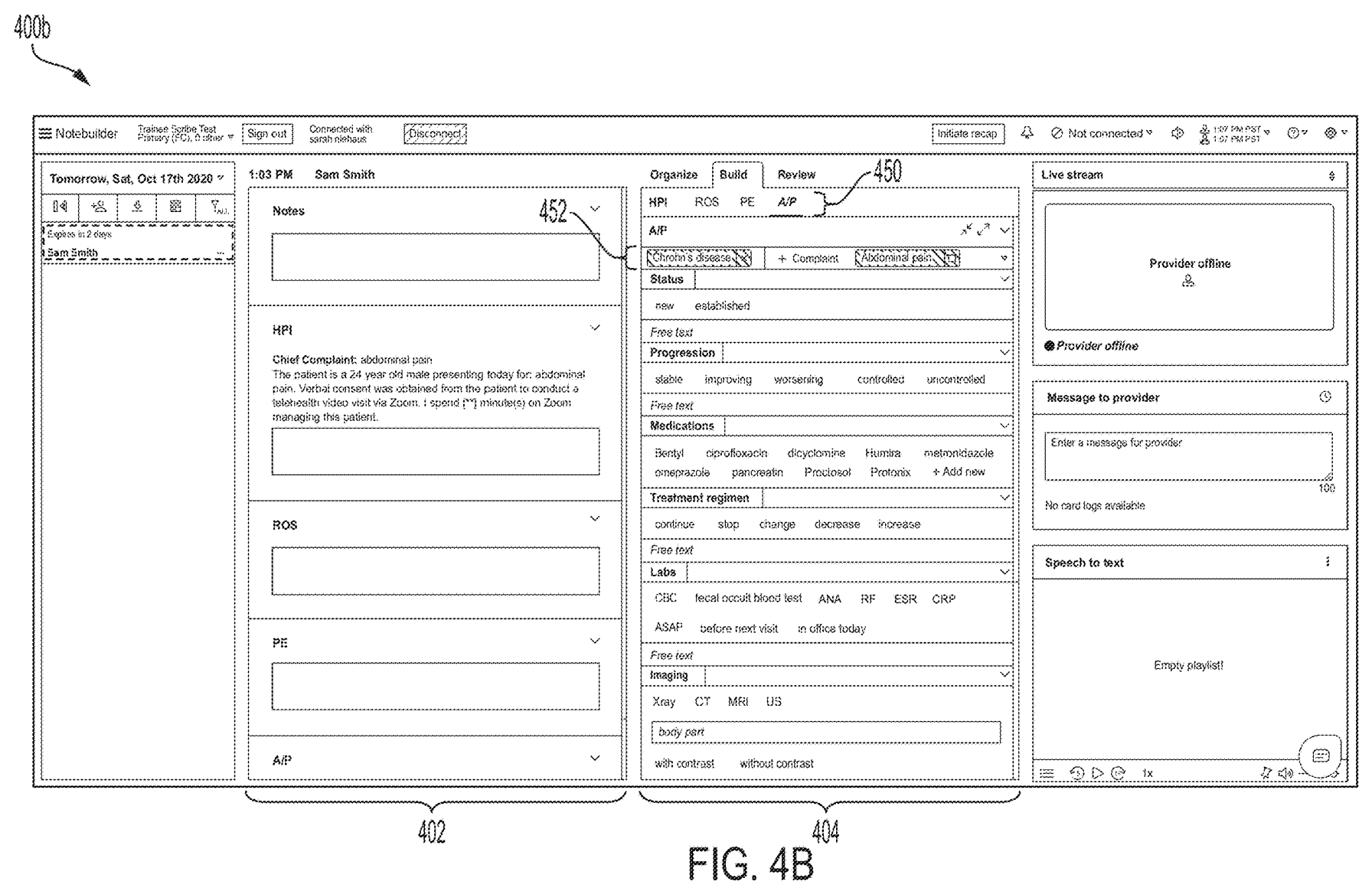

FIGS. 4A and 4B depict respective screens 400*a* and 400*b* of graphical user interface 400 of a natural-language medical record generation platform, in accordance with some embodiments. In some embodiments, GUI 400 may share any one or more characteristics in common with GUI 200 described above. Various functionalities of the systems and platforms disclosed herein are described below with reference to GUI screens 400*a* and 400*b*, with particular attention given to differences over features of GUI 200 as described above.

FIG. 4A depicts screen 400*a* of a graphical user interface 400, in accordance with some embodiments. Screen 400*a* depicts GUI 400 during the process of organizing or setting up the interface for capture of information during a patient visit. In some embodiments, screen 400*a* may share any one or more features in common with screen 200*b* of GUI 200, described above with reference to FIG. 2B.

Screen 400*a* may differ from screen 200*b* in that demographic information region 430 may comprise one or more additional GUI objects and be configured to accept one or more additional types of patient visit information as compared to demographic information region 230 of screen 200*b*. As shown in FIG. 4A, region 430 may comprise a set of selectable and/or deselectable icons/buttons for indicating a "visit type"; a set of selectable and/or deselectable icons/buttons for indicating a type of follow-up; a set of selectable and/or deselectable icons/buttons for indicating a service type (e.g., the type of patient visit being performed); a set of selectable and/or deselectable icons/buttons for indicating a platform via which the patient visit is being performed; and a field for indicating an amount of time spent on the patient visit.

In some embodiments, one or more of the sets of selectable and/or deselectable icons/buttons in region 430 may be displayed and/or hidden responsively to a selection made or other input executed by a user. For example, the options for indicating a follow-up type may be displayed in response to the user selecting the "follow-up" visit type icon/button. The options for indicating a platform type may be displayed in response to the user selecting the "telehealth" service type icon/button.

In some embodiments, the system may be configured such that GUI 400 requires selection of at least one option for a visit type. In some embodiments, the system may be configured such that GUI 400 requires selection of exactly one option for a visit type (or of at least one and no more than a predetermined maximum number of visit type options). In some embodiments, the selected "visit type" option may be used by the system to configure the template used to select and display one or more options for indicating medical information for a patient at a screen of GUI 400 for capturing medical information during the patient visit. In this way, the system may treat "visit type" as a special class of complaint types (e.g., a sub-class of complaint types), in that the system may use an indicated visit type in order to select sub-regions and GUI objects that are medically-relevant to the indicated visit-type. (In some embodiments, the "visit type" options may differ from "complaint" options in that the system may draw from different information sources to populate the available visit type options versus those used to populate available complaints.)

In some embodiments, one or more of the options selected (and/or user inputs otherwise indicated) in region 430 may be used to generate a natural-language statement for display in a canvas region of GUI 400 (e.g., a sentence may be generated stating the service type of the visit).

FIG. 4B depicts screen 400*b* of a graphical user interface 400, in accordance with some embodiments. Screen 400*b* depicts GUI 400 during the process of capturing of information during a patient visit (e.g., following a set-up/organize stage). In some embodiments, screen 400*b* may share any one or more features in common with screen 200*a* of GUI 200, described above with reference to FIG. 2A, and/or with screen 200*c*, described above with reference to FIG. 2C.

Screen 400*a* may include canvas region 402 and menu region 404, which may share one or more characteristics in common with canvas regions and menu regions, respectively, as described elsewhere herein. Screen 400*a* may differ from screens 200*a* and/or 200*c* in that menu region 404 may include note section navigation icons 450. As shown in FIG. 4B, navigation icons 450 may include an "HPI" (history of present illness) icon, a "ROS" (review of systems) icon, a "PE" (physical examination) icon, and an "A/P" (assessment/plan) icon. In some embodiments, selecting any one of the icons (e.g., by clicking or tapping the icon) in note section navigation icons 450 may cause GUI 400 to navigate to a corresponding portion of the note displayed in canvas region 402 and/or to display corresponding menu options in menu region 404. Thus, by clicking different navigation icons, a user may quickly navigate between different sections of the note and cause quick display of both the generated natural language note-contents and the GUI objects for inputting information relevant to that section of the note. In some embodiments, any one or more of the different sections of the interface for preparing note contents (e.g., HPI section, ROS section, PE section, A/P section) may share any one or more characteristics in common with one another.

In some embodiments, one or more GUI objects (e.g., selectable icons/buttons) splayed in a menu region of a GUI such as GUI 400 (or GUI 200) may be displayed in accordance with clinician preference and/or other back-end configurations. In some embodiments, one or more GUI options displayed in menu region 404 when the "ROS" or "PE" navigation icons are selected may be determined according to clinician preferences managed by back-end system configuration (e.g., rather than interactively/dynamically selected by a user of GUI 400).

As shown in FIG. 4B, menu region 404 may include A/P complaint selection sub-region 452. An A/P complaint selection sub-region may be a GUI region in which a user may input an indication of a complaint for which the A/P section of the menu region 404 is to be filled out. In some embodiments, a clinician or practitioner may have different assessment/plan information to enter for different patient complaints, or may intend to enter overlapping common assessment/plan information for two or more patient complaints. Accordingly, A/P complaint selection sub-region 452 may be auto-populated with options for selecting one or more complaints that were previously indicated at the setup stage (and/or for adding one or more new complaints) such that the user may flexibly indicate one or more complaints for which the user intends to enter assessment/plan information. In some embodiments, the A/P complaint selection sub-region 452 may additionally or alternatively allow a user to indicate a diagnosis. Indication of one or more complaints and/or diagnoses in sub-region 452 may cause GUI 400 to display one or more GUI objects in the A/P section of region 404 for entering information about the indicated complaints and/or diagnoses.

FIGS. 5A-5F depict respective screens of a graphical user interface (GUI) 500 of a system for configuring a natural-language medical record generation platform, in accordance with some embodiments. In some embodiments, GUI 500 may be displayed by a display of back-end user system 106 of system 100, such that a user of GUI 500 may execute inputs via GUI 500 in order to cause system 100 configure system 100 for providing platform (e.g., to a front-end user) for generating a natural-language entry (e.g., a note) pertaining to a patient visit for storage as part of an electronic health record. GUI 500 may, in some embodiments, be a back-end user interface for configuring functionality of system 100 and/or for configuring a front-end user-interface, such as GUI 200 and/or GUI 400, provided thereby. As described in detail below, a back-end user of GUI 500, such as a system administrator, may use GUI 500 to define a natural-language statement structure (e.g., a "sentence recipe" or "sentence formula") and to define and configure various GUI objects for use by a front-end user; the front-end user may then interact with the configured front-end interface to input patient information using the GUI objects defined and configured by the back-end user's inputs via GUI 500, and the system may accordingly generate a natural-language statement in accordance with the sentence structure defined by the back-end user's inputs via GUI 500. Various functionalities of the systems and platforms disclosed herein are described below with reference to GUI screens 500a-500f.

Figure 5A:
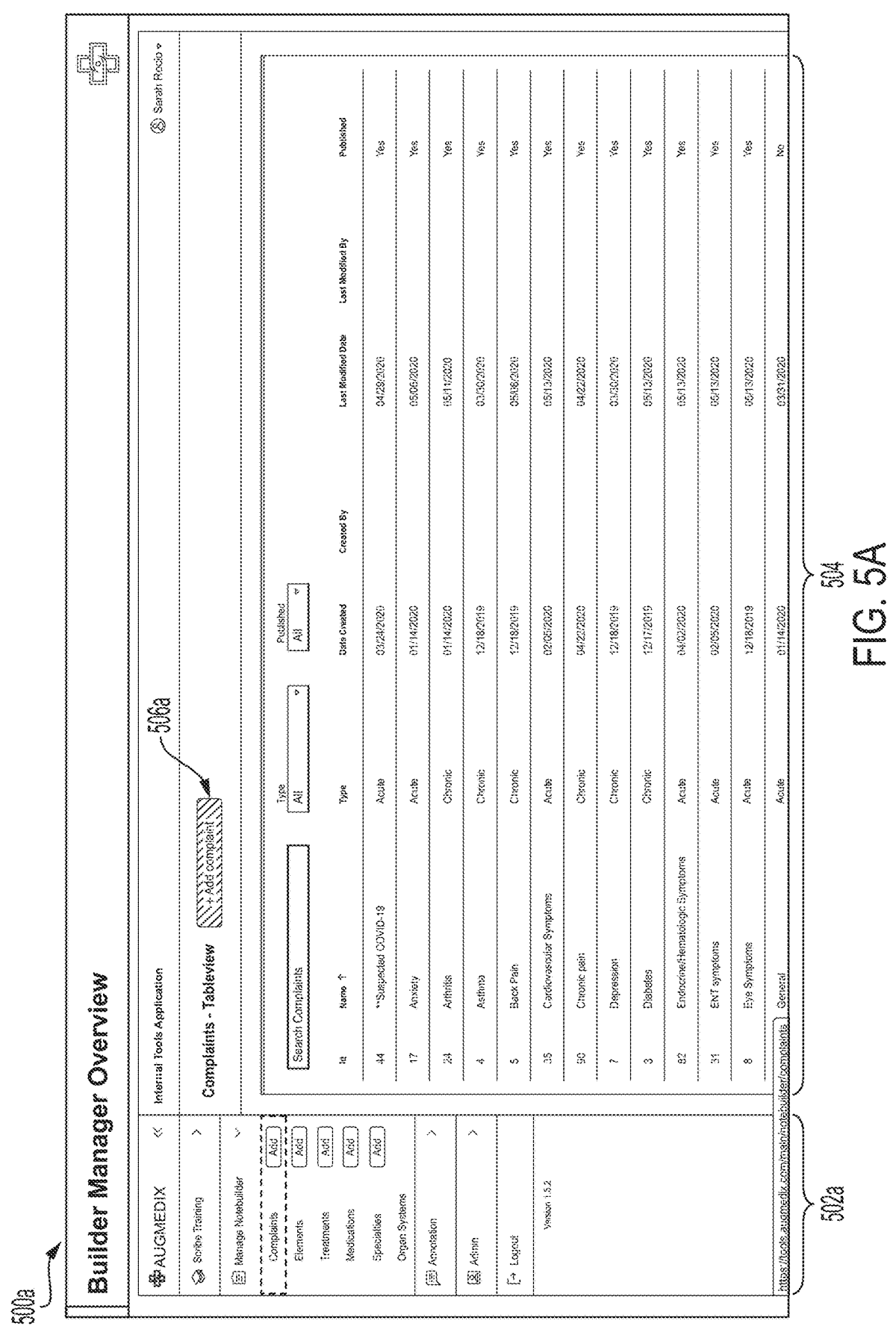

FIG. 5A depicts screen 500a of graphical user interface 500, in accordance with some embodiments. Screen 500a depicts GUI 500 during the process of displaying an overview of complaints to the user. As shown in FIG. 5A, screen 500a comprises components menu region 502a and complaints menu region 504.

Components menu region 502a may include a displayed menu (e.g., list) of GUI objects (e.g., selectable icons) corresponding to a plurality of components for use by a back-end user of the system in configuring the system to provide a platform for creating natural-language medical-record entries. As used herein, components of the back-end interface (e.g., GUI 500) may refer to categories of data that are used by the system to define data structures for creating, configuring, and providing the front-end interface. Components may include data that may be used by the back-end user to define GUI objects, natural-language statement structures, and/or filters and other logic for determining which options are presented to front-end users via the front-end interface for medical record entry generation. As shown in the example of components menu region 502a, components in some embodiments may include complaints, complaint elements, treatments, medications, and/or specialties.

In some embodiments, by selecting one of the components in components menu region 502a, the user may cause the system to provide one or more GUI screens by which the user may define instances of the selected component, for example by adding or defining complaints that are available in the system, by adding or defining medications that are available in the system, or the like.

In some embodiments, complaints that are added to the system may define a data structure that can be used by the system as a template for (a) providing a plurality of front-end GUI menu options for collecting medical information that is defined by the complaint data structure as being medically relevant to said complaint and (b) defining a plurality of natural-language statement structures that may incorporate information collected via inputs through said front-end GUI in order to generate and display natural-language statements for storage in an electronic health record.

In some embodiments, complaint elements that are added to the system may define an aspect of medical information for which information pertinent to a complaint may be collected. For example, a complaint element may include "symptoms," "onset mode and timing," "timing," "frequency," etc. The complaint element may be associated by the system with one or more options for manners in which a front-end user may enter input indicating medical information corresponding to the complaint element. In some embodiments, a complaint element may define a set of options that may displayed to a front-end user, for example as icons/buttons, and that may be selected and/or deselected by the front-end user in order to enter medical information pertinent to the complaint element. In some embodiments, a complaint may define a manner in which front-end information entered into the system and associated with a complaint element should be incorporated into one or more natural-language statements generated by the system; this manner may include a sentence recipe defined by a back-end user using GUI 500.

In some embodiments, treatments that are added to the system may define one or more treatment options that may be presented to a front-end user of the system for optional selection by the front-end user. In configuring a complaint and complaint element, a back-end user of GUI 500 may select one or more treatment options and thereby configure the system to present the selected options to the front-end user in association with the complaint and complaint element. Selection of a treatment option by a front-end user of the system may cause the system to (a) dynamically determine one or more GUI objects to be displayed and/or suppressed from display for the front-end user, in accordance with the option selected, and/or (b) incorporate the selected treatment option into a natural-language statement generated by the system, for example in accordance with a sentence recipe defined by the back-end user as part of the data structure associated with the complaint.

In some embodiments, medications that are added to the system may define one or more medication options that may be presented to a front-end user of the system for optional selection by the front-end user (e.g., to indicate a medication the patient is currently taking, has previously taken, or that is being prescribed to the patient). In configuring a complaint and complaint element, a back-end user of GUI 500 may select one or more medication options and thereby configure the system to present the selected options to the front-end user in association with the complaint and complaint element. Selection of a medication option by a front-end user of the system may cause the system to (a) dynamically determine one or more GUI objects to be displayed and/or suppressed from display for the front-end user, in accordance with the option selected, and/or (b) incorporate the selected medication option into a natural-language statement generated by the system, for example in accordance with a sentence recipe defined by the back-end user as part of the data structure associated with the complaint.

In some embodiments, specialties that are added to the system may define one or more medical specialties that may be presented to a front-end user of the system for optional selection by the front-end user, for example to allow the user to filter complaint options by medical specialty. In some embodiments, one or more additional filter components in addition to or alternatively to specialties may be configurable via screen 500*a*.

In some embodiments, a GUI 500 may include menu options for one or more additional or alternative components, including but not limited to labs, procedures, and imaging. Users of GUI 500 may select said options to define datasets for said components that may be used as building-blocks for complaint component option sets and/or used as filter components for filtering complaints.

As shown in FIG. 5A, complaints menu region 504 may display a plurality of complaints stored in the system. As described above, a complaint entered into the system via GUI 500 may be associated with a data structure that defines the manner in which the system renders and presents the front-end GUI to a user who indicates that a patient has presented with said complaint, and may further define the manner in which the system generates and stores a natural-language statement regarding said complaint and based on said front-end user's inputs.

As shown in FIG. 5A, complaints menu region 504 may display, for a given complaint, an identifier (e.g., unique identifier such as ID number), name, type, creation date, creator, last modification date, most recent modifier, and publication status.

Screen 500*a* may additionally include new complaint icon 506*a* for causing the system to generate and store a data structure for a new complaint. By selecting new complaint icon 506*a* or selecting a preexisting complaint in complaints menu region 504, a user may cause the system to display one or more screens of GUI 500 for configuring system functionality associated with the complaint, as described in further detail below.

Figure 5B:
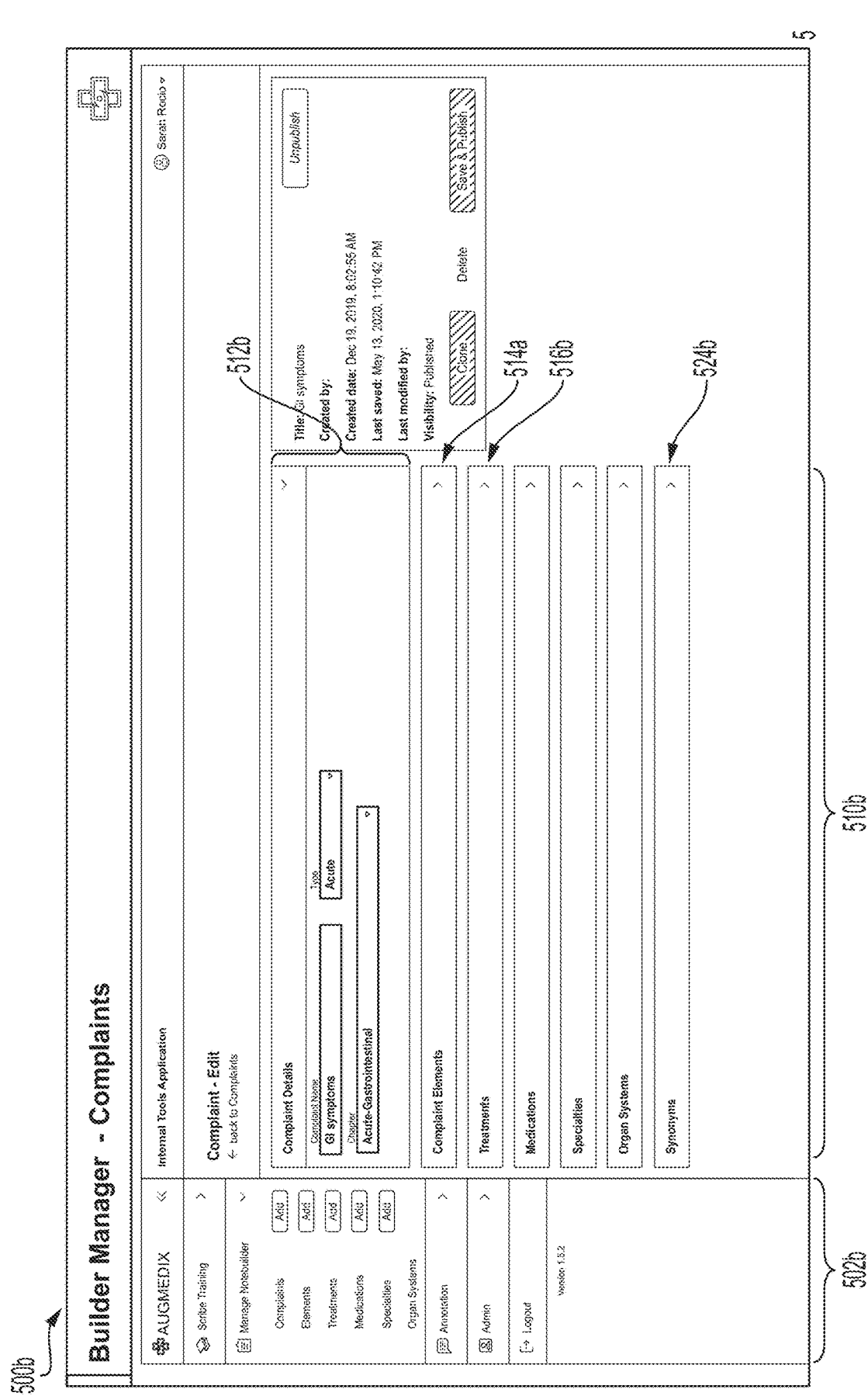

FIG. 5B depicts screen 500*b* of graphical user interface 500, in accordance with some embodiments. Screen 500*b* depicts GUI 500 during the process of editing (e.g., creating or modifying) a complaint such that data structure may be stored for allowing the system to (a) provide a front-end GUI for accepting front-end user inputs regarding medical information for a patient presenting with said complain1 and (b) generate and store a natural-language statement in accordance with inputs entered into the front-end GUI by the front-end user. As shown in FIG. 5B, screen 500*b* comprises components menu region 502*b* and complaint editing region 510*b*. Components menu region 502*b* may share any one or more features in common with components menu region 502*a*, described above with reference to FIG. 5A.

Complaint editing region 510*b* may be a region of GUI 500 configured to allow a back-end user to execute various inputs for configuring data structures associated with the complaint being edited, such that the system may use said configured data structures to provide front-end interfaces associated with said complaints and configured to collect medical information regarding patients presenting with said complaint and to generate natural-language statements based on said collected information.

As shown in FIG. 5B, complaint editing region 510*b* may include various sub-regions for editing different information about the complaint, including: complaint details sub-region 512*b*, complaint elements sub-region 514*b*, treatments sub-region 516*b*, and synonyms sub-region 524*b*. In some embodiments, one or more of the sub-regions may provide access to a back-end user of GUI 500 to one or more GUI objects included therein that allow the user to execute inputs to configure information pertaining to the subject matter of the respective sub-region. Thus, complaint details sub-region 512*b*, as shown, may contain one or more GUI objects (e.g., text fields, drop-down menus, etc.) configured to allow a user to execute inputs to specify information about details about the complaint, such as a name for the complaint, a type for the complaint, and/or a chapter or other categorization for the complaint.

In some embodiments, one or more of the sub-regions may be expandable and collapsible to show or hide GUI objects contained therein; in FIG. 5B, sub-region 512*b* is shown in the expanded state and the other sub-regions are shown in the collapsed state.

Figure 5C:
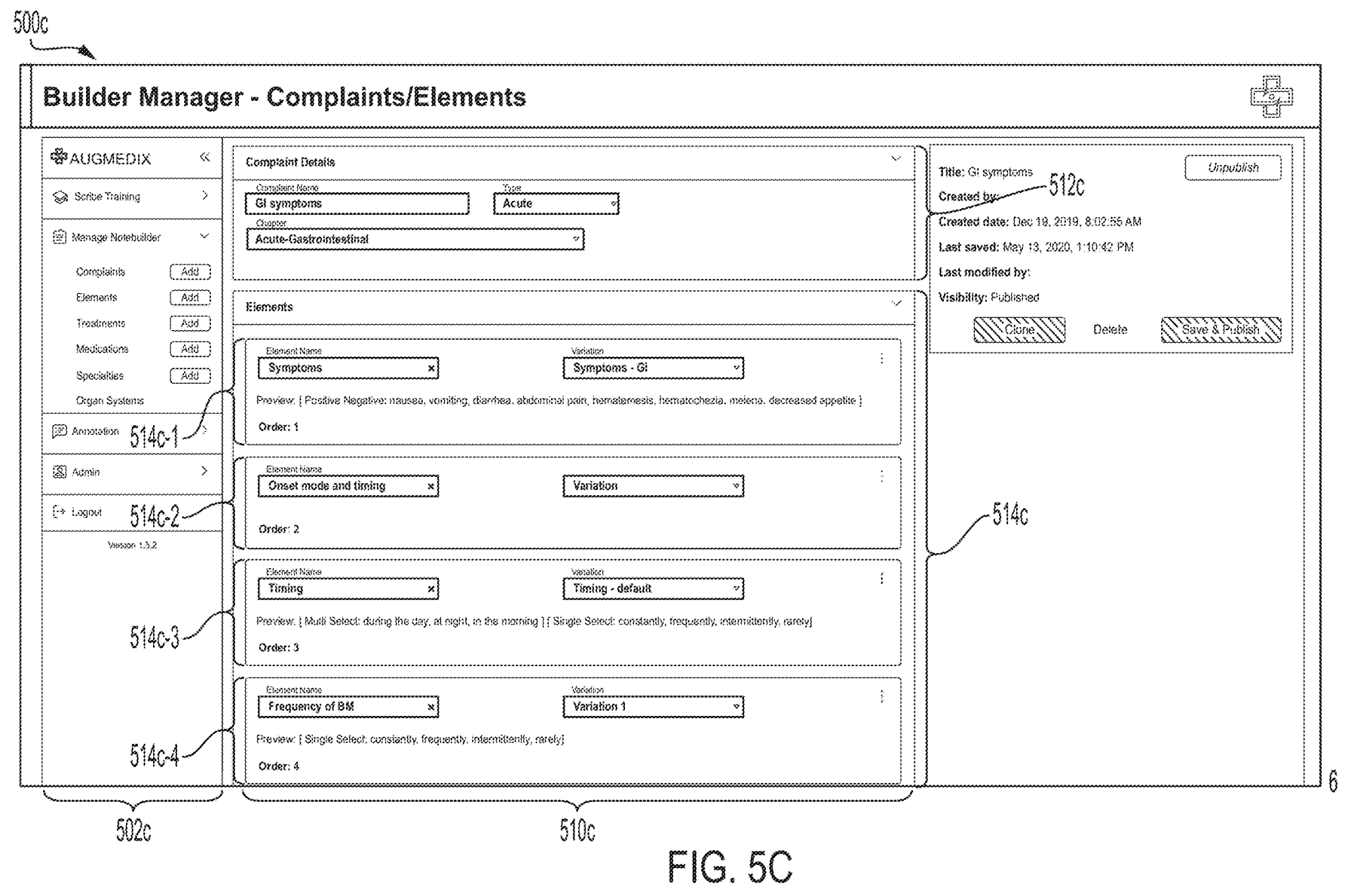

FIG. 5C depicts screen 500*c* of graphical user interface 500, in accordance with some embodiments. Screen 500*c* depicts GUI 500 during the process of editing (e.g., creating or modifying) complaint elements of a complaint (with complaint elements sub-region 514*c* in an expanded state). As shown in FIG. 5C, screen 500*c* comprises components menu region 502*c*, complaint editing region 510*c*, complaint details sub-region 512*c*, and complaint elements sub-region 514*c*. Screen 500*c* may be a screen of GUI 500 that differs from screen 500*b* in that the complaint elements sub-region has been expanded and the complaint editing region has been scrolled down; components, features, or aspects of screen 500*c* may share any one or more characteristics in common with corresponding components, features, or aspects of screen 500*b* described above with reference to FIG. 5B.

As shown in FIG. 5C, complaint elements sub-region 514*c* displays (in its expanded state) a plurality of complaint-element windows 514c-1, 514c.2, 514c-3, and 514c-4. Each of the complaint-element windows is configured to display information about a corresponding complaint element and/or to allow a user of GUI 500 to enter inputs to configure one or more aspects of the corresponding complaint element. As shown, the complaint-element windows may display GUI object indicating the name of the complaint-element (e.g., a type or class of complaint-element), a GUI object indicating a variation of the complaint-element (e.g., a sub-type or sub-class of the complaint element), a GUI object indicating preview information for one or more input fields and/or options associated with the complaint-element, and/or a GUI object associated with an order of the complaint-element.

In some embodiments, the GUI object indicating preview information for one or more input fields and/or options associated with the complaint-element may display information indicating one or more options and/or one or more option groups. The options displayed may include selectable options that the system may render as selectable/deselectable icons/buttons on a front-end user interface, and said options may be arranged into one or more option groups. The GUI object indicating preview information may specify whether an option group is a single-select option group (e.g., requiring selection of no more than one, or of exactly one option) or a multi-select option group (e.g., requiring or allowing the selection of multiple options). The GUI object indicating preview information may specify whether options in an option group are merely positively selectable or whether the option is also deselectable (e.g., able to be indicated as deselected).

In some embodiments, the GUI object indicating order information for the complaint-element may indicate an order in which a front-end GUI sub-region associated with the complaint-element will be rendered by the system on the front-end GUI. In some embodiments, a back-end user of GUI 500 may modify the order of complaint-elements, for example by dragging and dropping complaint-element windows into a different order in complaint-elements sub-region 510c.

In some embodiments, one or more of the GUI objects displayed in a complaint-element window may be passive in that it may passively display information, or may be interactive in that a user may be able to interact with the GUI object to execute input specifying information regarding the complaint element (such as by typing information or selecting options from a drop-down menu). In some embodiments, additionally or alternatively to enabling a user to execute inputs for configuring a complaint-element directly via one of the GUI objects of one of the complaint-element windows (514c-1, 514c.2, 514c-3, and/or 514c-4), GUI 500 may be configured to allow a back-end user to execute inputs for configuring a complaint-element via a one or more separate screens of GUI 500, as discussed in further detail below. In some such embodiments, a user may select a complaint element (e.g., by clicking or tapping on a corresponding complaint-element window) to open a screen for configuring the specific complaint-element.

Figure 5D:
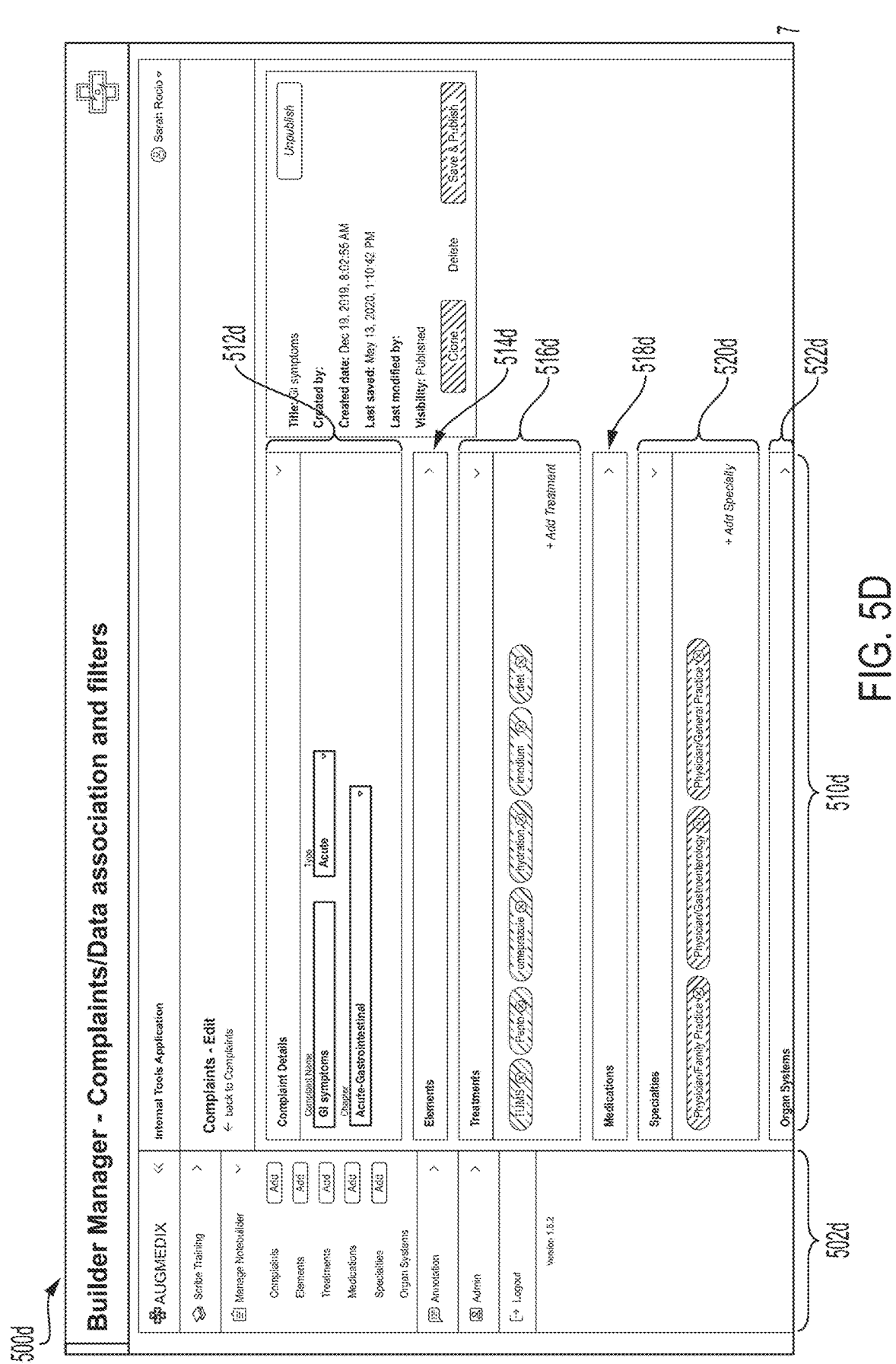

FIG. 5D depicts screen 500d of graphical user interface 500, in accordance with some embodiments. Screen 500d depicts GUI 500 during the process of editing (e.g., creating or modifying) complaint elements of a complaint (with complaint elements sub-region 514d in an expanded state, treatments sub-region 516d in an expanded state, and specialties sub-region 520d in an expanded state). As shown in FIG. 5D, screen 500d comprises components menu region 502d, complaint editing region 510d, complaint details sub-region 512d, complaint elements sub-region 514d, treatments sub-region 516d, medications sub-region 518d, specialties sub-region 520d, and organ systems sub-region 522d. Screen 500d may be a screen of GUI 500 that differs from screen 500b in that the treatments sub-region has been expanded, the specialties sub-region has been expanded, and the complaint editing region has been scrolled down; components, features, or aspects of screen 500d may share any one or more characteristics in common with corresponding components, features, or aspects of screen 500b and/or screen 500c described above with reference to FIG. 5B and FIG. 5C respectively.

As shown in FIG. 5D, treatments sub-region 516d displays (in its expanded state) a plurality of GUI objects each indicating a treatment option. In some embodiments, the GUI objects indicating a treatment option may be provided as icons that may be added to or removed from treatments sub-region 516d by a user of GUI 500. For example, to add a new treatment option, a user may drag a treatment option into treatments sub-region 516d, click or tap an icon/button for adding a new treatment option, and/or select a treatment option to be added from a menu. In some embodiments, to remove a treatment option from treatments sub-region 516d, a user may drag the icon representing the option out of treatments sub-region 516d and/or select an affordance (e.g., an "X" icon) to delete the icon representing the option.

In some embodiments, the system may be configured such that treatment options added to treatments sub-region 516d by the user are associated with (e.g., incorporated into) the data structures representing the complaint being configured. In some embodiments, the system may be configured to use to indicated treatment options to populate (e.g., as suggestions) the front-end user interface with corresponding options for prescribing the indicated treatment options for a patient.

As shown in FIG. 5D, specialties sub-region 520d displays (in its expanded state) a plurality of GUI objects each indicating a medical specialty. In some embodiments, the GUI objects indicating a medical specialty may be provided as icons that may be added to or removed from specialties sub-region 520d by a user of GUI 500. For example, to add a new medical specialty, a user may drag a medical specialty into specialties sub-region 520d, click or tap an icon/button for adding a new medical specialty, and/or select a medical specialty to be added from a menu. In some embodiments, to remove a medical specialty from specialties sub-region 520d, a user may drag the icon representing the specialty out of specialties sub-region 520d and/or select an affordance (e.g., an "X" icon) to delete the icon representing the specialty.

In some embodiments, the system may be configured such that medical specialties added to specialties sub-region 520d by the user are associated with (e.g., incorporated into) the data structures representing the complaint being configured. In some embodiments, the system may be configured to use to indicated medical specialties as filters by which a front-end user of a front-end GUI may filter available complaints in order to locate and select a desired complaint.

Figure 5E:
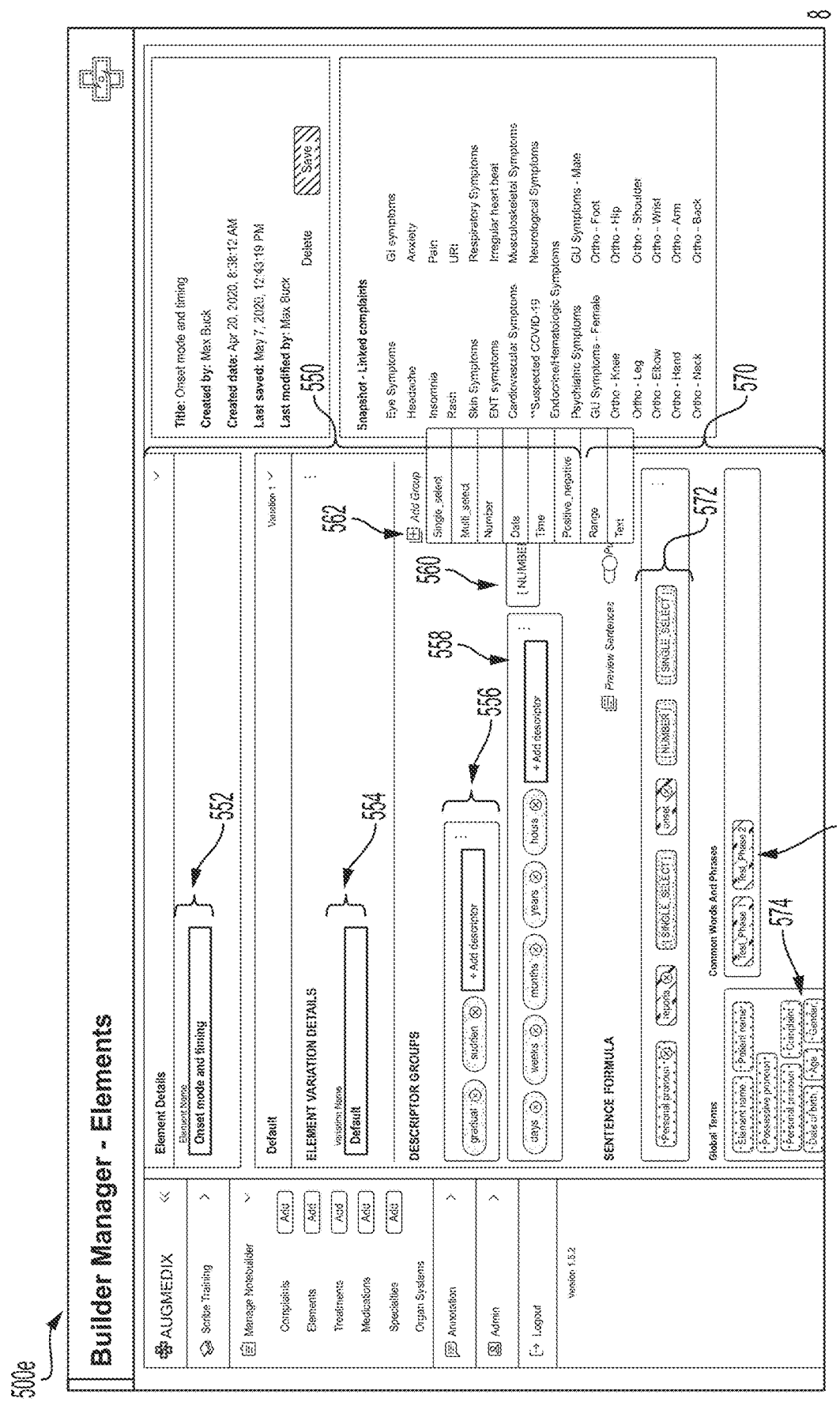

FIG. 5E depicts screen 500e of graphical user interface 500, in accordance with some embodiments. Screen 500e depicts GUI 500 during the process of editing (e.g., creating or modifying) a complaint element. In some embodiments, a user may access screen 500e in order to modify a complaint element by selecting (e.g., clicking or tapping on) an existing complaint element window at screen 500c and/or by selecting an affordance at screen 500c indicating an instruction to create a new complaint-element. As shown in FIG.

5E, screen 500e comprises complaint-element editing region 550 and sentence formula region 570, each of which are described in further detail below.

Complaint-element editing region 550 may be configured to display information about a complaint-element and to allow a user of GUI 500 to execute one or more inputs comprising instructions to configure one or more aspects of the complaint-element being edited.

Complaint-element editing region 550 may include complaint-element name sub-region 552, which may display information regarding a name of the complaint-element (e.g., a type or class of complaint-element). The system may be configured such that a user may execute one or more inputs via complaint-element name sub-region 552 (e.g., by typing in a field and/or selecting one or more options, such as from a drop down menu) to specify a name for the complaint-element.

Complaint-element editing region 550 may include complaint-element variation sub-region 554, which may display information regarding a variation of the complaint-element (e.g., a sub-type or sub-class of the complaint-element). The system may be configured such that a user may execute one or more inputs via complaint-element variation sub-region 554 (e.g., by typing in a field and/or selecting one or more options, such as from a drop down menu) to specify a variation for the complaint-element.

Complaint-element editing region 550 may include descriptor-group sub-regions 556 and 558. In some embodiments, a descriptor-group sub-region may be configured to display a plurality of options for describing or characterizing the complaint-element. For example, FIG. 5E shows an example in which the complaint-element being configured pertains to onset mode and timing of a system, and descriptor group sub-region 556 includes options for characterizing onset mode as either "gradual" or "sudden," while descriptor group sub-region 558 includes options for characterizing the onset timing by a unit of time such as "days," "weeks," "months," etc. (Descriptor group 558 is also associated with field signifier 560, which signified a field configured to accept input of a number to be associated with the descriptor-group options shown in descriptor-group sub-region 558.

In some embodiments, interface 500 may allow a back-end user to add or remove options from a descriptor group sub-region in order to configure which selectable/deselectable icons are displayed to a front-end user of a front-end GUI for inputting patient information. In some embodiments, a back-end user may be able to drag and drop or otherwise add and remove options from a descriptor group sub-region, such that options that are included therein will be displayed as front-end selectable/deselectable icons and such that options that are not included therein will not be displayed on the front end.

As shown in FIG. 5E, a back-end user may optionally add one or more field indicators in association with a descriptor group, such as field indicator 560 which is associated with descriptor group sub-region 558. By adding field indicator 560 to complaint-element editing region 550, the back-end user may configure the system such that a field for accepting input of a number is displayed, via the front-end GUI, in association with the set of selectable/deselectable icons pertaining to onset timing. In some embodiments, a user may be able to specify whether a field such as field indicator 560 is configured to accept numbers, free-text, or both.

In some embodiments, a user may be able to add a single-select descriptor group (e.g., a descriptor group configured to allow selection/deselection of one option), a multi-select descriptor group (e.g., a descriptor group configured to allow selection/deselection of multiple options), a number field or number menu, a date field or date menu, a time field or time menu, a positive/negative GUI object indicator, a range GUI object indicator, and/or a free text field. As shown in FIG. 5E, a user may in some embodiments select the "add group" icon 562 in order to add one or more of said GUI features to complaint-element editing region 550. In some embodiments, any one or more of said GUI features (e.g., field indicators, menu indicators, and/or descriptor groups) all may be treated by GUI 500 and treated by the system as "groups" that may be added while configuring a complaint-element at screen 500e; and any one or said GUI features added as a group to screen 500e may be associated with a front-end GUI object (e.g., field, menu, or group of icons) configured to accept user input regarding patient information associated with the complaint element.

In some embodiments, a back-end user may be able to add any suitable number of said "groups" (e.g., field indicators, menu indicators, and/or descriptor groups) to GUI screen 500e. In some embodiments, a user may be able to arrange the order and/or grouping of said "groups," and the system may be configured such that the order and/or grouping specified by the back-end user is mirrored by associated GUI objects provided on the corresponding front-end GUI.

In addition to complaint-element editing region 550, GUI screen 500e may additionally include sentence formula region 570, which may be configured to allow a back-end user of GUI 500 to define and configure a natural-language statement structure by configuring a visual representation 572 of a sentence (or statement). The system may be configured such that the natural-language statement structure defined in accordance with visual representation 572 may be used by the system to generate and store a natural-language statement confirming to the structure and based at least in part on inputs entered by the front-end user via the front-end GUI.

As shown in the example in FIG. 5E, the visual representation 572 may include a plurality of icons that can be rearranged to define an order of sentence parts. Each icon defining a sentence par may define one or more of fixed word/phrase or a dynamic word/phrase. A fixed word or phrase may be inserted into the statement at the specified space regardless of user input, whereas a dynamic word/phrase may represent a part of the sentence that may be updated in accordance with front-end user input.

In visual representation 572, the "personal pronoun" icon may represent a dynamic word/phrase that causes the system to generate and insert a pronoun for the patient into a natural language statement being generated, wherein the pronoun is selected in accordance with front-end user input specifying a gender for the patient and/or explicitly specifying a pronoun for the patient.

In visual representation 572, the "reports" icon may represent a static word/phrase that causes the system to generate and insert the word "reports" into the natural language statement being generated.

In visual representation 572, the first "[SINGLE_SELECT]" icon may represent a dynamic word/phrase that causes the system to generate and insert a word or phrase into the natural language statement being generated, wherein word or phrase is selected based on a user selection made by the front-end user of one or more of the available options in a descriptor group associated with the first "[SINGLE_SELECT]" icon. In this case, the associated descriptor group is the group of options represented by descriptor-group sub-region 556. Thus, for example, if the front-end user selects the option for "gradual" onset, then the word "gradual" may be inserted in the generated natural-language statement.

In visual representation 572, the "onset" icon may represent a static word/phrase that causes the system to generate and insert the word "onset" into the natural language statement being generated.

In visual representation 572, the "[NUMBER]" icon may represent a dynamic word/phrase that causes the system to generate and insert a word or phrase into the natural language statement being generated, wherein word or phrase is selected based on a user indication made by the front-end user of a number, via either a number field or a number menu provided to the front-end user in association with the back-end user's placement of number field signifier 560 into complaint-element editing region 550. Thus, for example, if the front-end user enters the number "3" into a number field provided by the front-end GUI, then the word "three" or the number "3" may be inserted in the generated natural-language statement.

In visual representation 572, the second "[SINGLE_SELECT]" icon may represent a dynamic word/phrase that causes the system to generate and insert a word or phrase into the natural language statement being generated, wherein word or phrase is selected based on a user selection made by the front-end user of one or more of the available options in a descriptor group associated with the second "[SINGLE_SELECT]" icon. In this case, the associated descriptor group is the group of options represented by descriptor-group sub-region 558. Thus, for example, if the front-end user selects the option for onset over a number of "weeks," then the word "weeks" may be inserted in the generated natural-language statement.

In some embodiments, a user of GUI screen 500e may execute one or more commands to create and configure an icon for inclusion in visual representation 572, including by specifying its placement in visual representation 572, its association with one or more "groups" from complaint-element editing region 550, and the manner in which it is displayed and/or labeled in visual representation 572.

In some embodiments, a user of GUI screen 500e may be able to automatically generate an icon for inclusion in visual representation 572 by selecting (e.g., clicking and dragging) one or more of the options from global terms sub-region 574. The global terms options displayed in global terms sub-region 574 may be preconfigured with respective label and display characteristics for use in visual representation 572 and with respective associated rules for generating dynamic words/phrases for the respective global terms option. For example, the "element name" global term option may be configured to cause the name of the associated element to be inserted into the generated natural-language statement; the "patient name" global term option may be configured to cause the patient's name (e.g., as indicated by front-end user inputs executed via a demographic information input function of the front-end GUI) to be inserted into the generated natural-language statement.

In some embodiments, a user of GUI screen 500e may be able to automatically generate an icon for inclusion in visual representation 572 by selecting (e.g., clicking and dragging) one or more of the options from common words/phrases sub-region 576. The common words/phrases options displayed in common words/phrases sub-region 576 may be preconfigured with respective label and display characteristics for use in visual representation 572 and with respective associated rules for generating a respective static word/phrase.

Figure 5F:
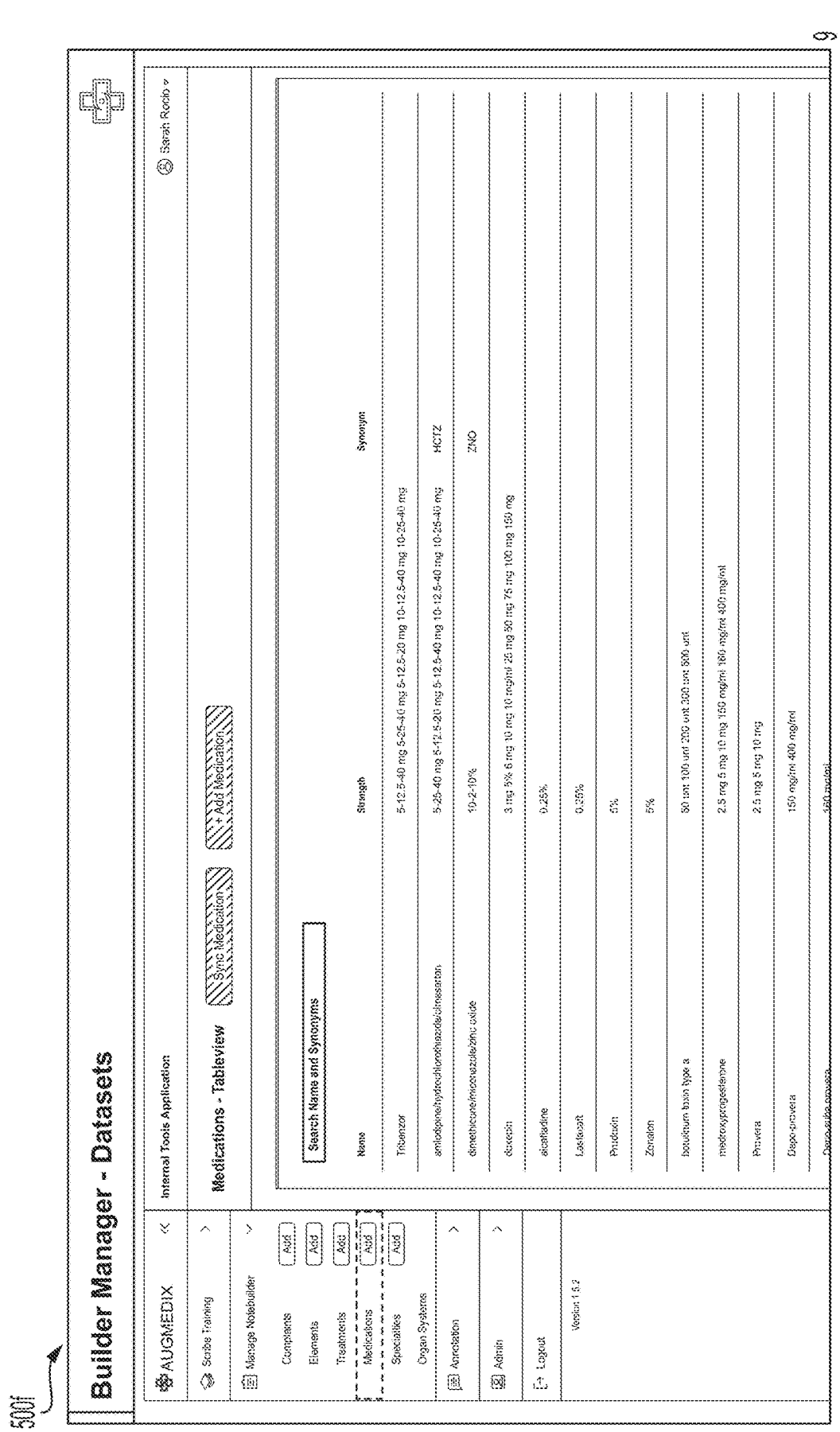

FIG. 5F depicts screen 500f of graphical user interface 500, in accordance with some embodiments. Screen 500f depicts GUI 500 during the process of managing (e.g., creating, viewing, or modifying) one or more datasets. Datasets used by the system may include datasets of treatments, medications, specialties, or organ systems. In some embodiments, a user may access screen 500f in order to review, input, or configure a dataset that is accessible by the system.

In some embodiments, datasets may be used by the system to configure an interface for a complaint, such as a front-end GUI as discussed herein for inputting patient information. In some embodiments, data from one or more of the datasets uploaded into the system may be automatically associated, in whole or in part, with one or more complaints. For example, a front-end interface may be configured such that a certain list taken from one or more datasets—e.g., a certain list of medications—is used to populate options displayed to a front-end user. In some embodiments, a back-end interface may be configured such that a certain list taken from one or more of the datasets may be used to populate suggested options to be selected by the back-end user for inclusion in the front-end interface. In some embodiments, a back-end user may at an initial stage associate one or more items in a dataset with one or more symptoms, complaints, or the like, and the stored association may be used at a future time to display or suggest one or more options to a different back-end user.

In some embodiments, medical dataset information may include medication names, medication dosages, medication side-effects, medication interactions, and/or medication synonyms.

Figure 6:
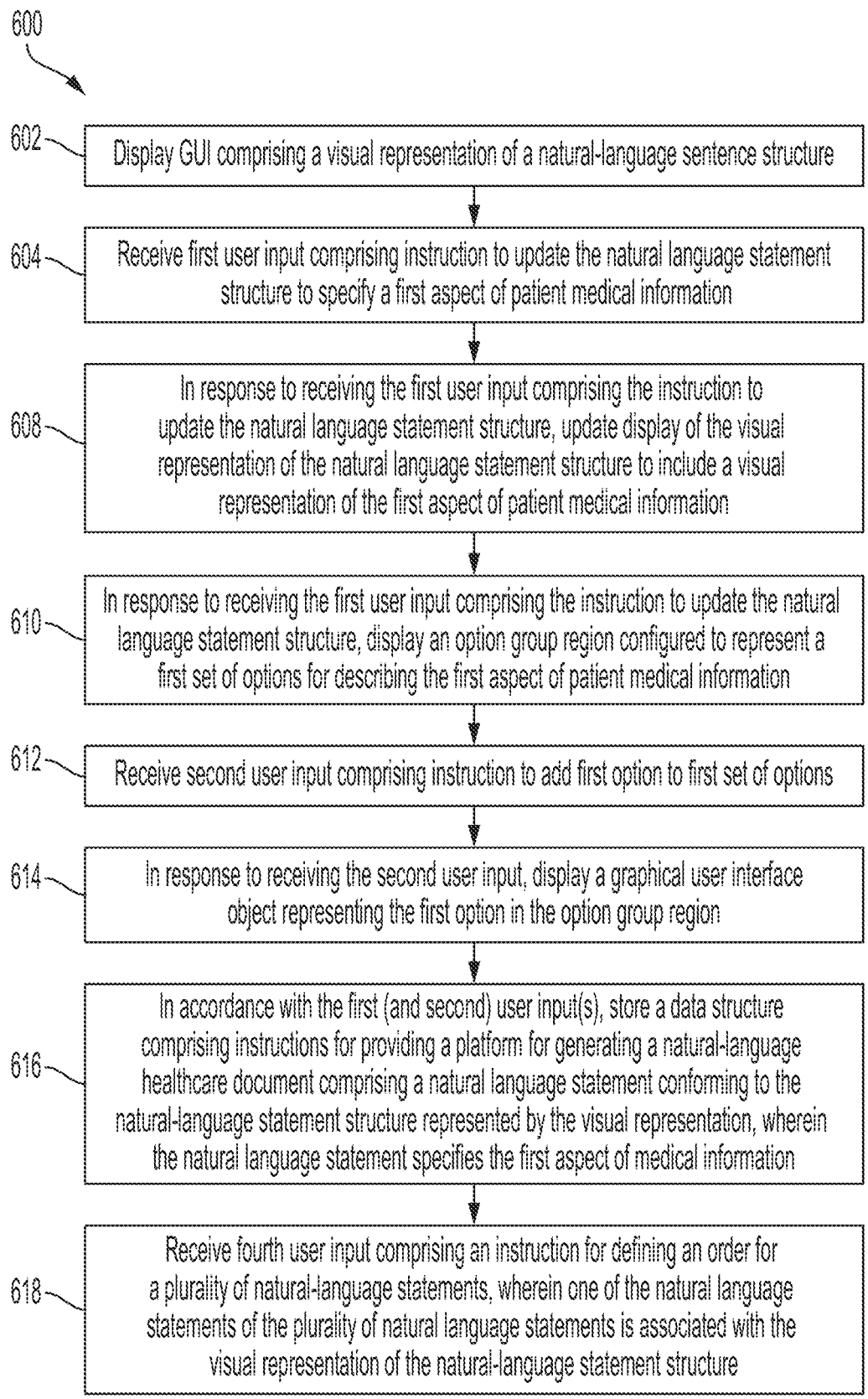
FIG. 6 depicts a flow chart describing a method for configuring a natural-language medical record generation platform, in accordance with some embodiments.

FIG. 6 depicts a flow chart describing method 600 for providing a system for configuring a natural-language medical record generation platform, in accordance with some embodiments. In some embodiments, method 600 may be performed by a system for providing a natural-language medical record generation platform, such as system 100 described above with reference to FIG. 1. As described below, method 600 may include providing one or more back-end GUI screens for accepting back-end user inputs for configuring and deploying front-end GUI's, wherein the configured front-end GUI's are configured to collect patient information to automatically generate one or more natural-language statements based thereon. The manner in which the front-end GUI collects patient information and the manner in which the system incorporates the collected patient information into a natural-language statement structure may be defined by back-end user inputs made to said back-end GUI. In some embodiments, the one or more back-end GUI screens displayed in method 600 may include (or may share one or more features in common with) one or more of GUI screens 500a-500f described above in FIGS. 5A-5F.

At block 602, in some embodiments, the system may display a graphical user interface comprising a visual representation of a natural-language statement structure. In some embodiments, the graphical user interface may be a back-end graphical user interface configured to allow back-end users to configure a platform for automatically generating natural-language statements regarding patient medical information, wherein the back-end user interface is configured to allow back-end users to both (a) define a natural-language sentence structure to be used by the platform in automatically generating a natural-language statement and (b) define one or more sets of options to be displayed to the front-end user to facilitate the receipt of front-end user inputs to define patient medical information for integration into said automatically-generated natural language statement. In some embodiments, the graphical user interface displayed at block 602 may be GUI screen 500*e*, wherein the displayed visual representation of a natural-language statement structure is visual representation 572.

At block 604, in some embodiments, the system may receive a first user input comprising an instruction to update the natural language statement structure to specify a first aspect of patient medical information. The system may receive any data representing a user input comprising an instruction to update the natural language statement structure. In some embodiments, a user may execute an input indicating an instruction to update the natural language statement structure by interacting with one or more GUI objects (e.g., text fields, drop-down menus, check-boxes, selectable and/or deselectable buttons/icons, click-and-drag icons, lists, other menus, or the like).

In some embodiments, the first aspect of patient medical information that may be described in accordance with selection (or deselection) of an option may include: a symptom, onset mode of a symptom, onset timing of a symptom, timing or frequency information, location of a symptom, contextual information, quality of a symptom, a prior or current medical condition, a diagnosis, a prior or current medication, a medication to be prescribed, a prior or current treatment, a treatment to be prescribed, prior or current lab tests, lab tests to be ordered, lab test results information, prior or current imaging procedures, imaging procedures to be ordered, imaging procedure results information, an organ system, a prior or current diagnostic procedure, a diagnostic procedure to be prescribed, results of a diagnostic procedure, prior or current treatments, and/or a treatment to be prescribed.

In some embodiments, the first user input may be provided by the user adding an icon to the visual representation of the natural-language statement structure, such as by clicking a button or icon to instruct adding the new icon or by clicking and dragging a new icon into the visual representation. In some embodiments, the first user input may be provided by the user rearranging an icon within the visual representation of the natural-language statement structure (e.g., moving the icon to a new location in the visual representation structure), such as by clicking a button or icon to instruct the rearrangement or by clicking and dragging a preexisting icon in the visual representation to a new location in the visual representation.

In the example of screen 500*e* in FIG. 5E, a user of GUI 500 may have executed an instruction to add the leftmost "SINGLE_SELECT" icon to visual representation 572, for example by clicking or tapping "add group" icon 562 and/or by indicating a location within visual representation 572 for the leftmost "SINGLE_SELECT" icon to be added.

At block 606, in some embodiments, the system may, in response to receiving the first user input comprising the instruction to update the natural language statement structure, update display of the visual representation of the natural language statement structure to include a visual representation of the first aspect of patient medical information. For example, the system may update display of a visual representation of a sentence structure to insert or rearrange one or more displayed icons representing respective sentence parts. In the example of screen 500*e* in FIG. 5E, the system may update display of visual representation 572 to insert and/or place, for example, the leftmost "SINGLE_SELECT" icon in accordance with the first user input.

In addition to updating display of the visual representation, the system may update configuration of a corresponding front-end user interface such that the front-end interface is configured to generate a natural-language statement in accordance with the statement structure represented by the visual representation.

At block 608, in some embodiments, the system may, in response to receiving the first user input comprising the instruction to update the natural language statement structure, display an option group region configured to represent a first set of options for describing the first aspect of patient medical information. For example, when a executes an instruction to insert and/or place a representation of an sentence part in a visual representation of a natural-language sentence structure, the system may update display of the visual representation accordingly and may also display set of options corresponding to the updated or added sentence part. The set of options—which may each be represented, for example, by an item in a list or by a labeled icon—may be displayed in an option group region of the graphical user interface. As used herein, "option group" may refer to any group of options (or visual representations of options) displayed on a GUI such as back-end GUI 500. In the example of screen 500*e* in FIG. 5E, the system may display (or update display of) descriptor-group sub-region 556, which may be associated with the leftmost "SINGLE_SELECT" icon in visual representation 572, as explained above.

At block 610, in some embodiments, the system may receive a second user input comprising an instruction to add a first option to the first set of options. At block 612, in some embodiments, the system may, in response to receiving the second user input, display a graphical user interface object representing the first option in the option group region.

The system may receive any data representing a user input comprising an instruction to add a first option to the first set of options displayed in the option group. In some embodiments, the second input may be configured (alternatively or additionally) to a remove an option from the first set of options displayed in the option group. In some embodiments, a user may execute an input indicating an instruction to add an option to an option group by interacting with one or more GUI objects (e.g., text fields, drop-down menus, check-boxes, selectable and/or deselectable buttons/icons, click-and-drag icons, lists, other menus, or the like).

In some embodiments, the second user input may be provided by the user typing into a text field to search for available descriptors to be added as options to an option group. In the example of screen 500*e*, the user may type into the "add descriptor" text field in descriptor-group sub-region 556 to search for additional descriptors to be added to descriptor-group sub-region 556. In some embodiments, a user may click the "X" icon on a displayed icon in descriptor-group sub-region 556 in order to remove the icon from descriptor-group sub-region 556 and thereby remove the option from the option group.

In some embodiments, the second user input may comprise an instruction to configure the set of options such that a user of the front-end interface is required to select a predetermined number of options from the set, no more than a predetermined number of options from the set, or no less than a predetermined number of options from the set. In some embodiments, the second user input may comprise an instruction to configure the set of options such that a user of the front-end interface is required to select only one option from the set. In some embodiments, the second user input may comprise an instruction to configure the set of options such that a user of the front-end interface is required to select multiple options from the set.

In some embodiments, the second user input may comprise an instruction to configure the set of options such that a user of the front-end interface may positively select one or more of the options. In some embodiments, the second user input may comprise an instruction to configure the set of options such that a user of the front-end interface may negatively indicate (e.g., "deselect") one or more of the options. In some embodiments, the second user input may comprise an instruction to configure the set of options such that a user of the front-end interface may leave one or more of the options as neither selected nor deselected.

At block 614, in some embodiments, the system may, in accordance with the first and/or second user input(s), store a data structure comprising instructions for providing a platform for generating a natural-language healthcare document comprising a natural language statement conforming to the natural-language statement structure represented by the visual representation, wherein the natural language statement specifies the first aspect of medical information.

In accordance with the first user input, in addition to updating display of the visual representation, the system may update configuration of a corresponding front-end user interface such that the front-end interface is configured to generate a natural-language statement in accordance with the statement structure represented by the visual representation.

In accordance with the first user input, in addition to updating display of the visual representation, the system may update configuration of the corresponding front-end user interface such that the front-end interface is configured to display a set of selectable options (e.g., selectable/deselectable icons) corresponding to the set of options included in the option group on the back-end interface.

In this manner, the back-end user may use the back-end GUI to configure both the natural-language statement structure and the options available to the front-end user when the front-end GUI is deployed.

In some embodiments, the system may update configuration of the platform for providing the front-end GUI automatically as the back-end user executes inputs to the back-end GUI. In some embodiments, the system may update configuration of the front-end GUI in accordance with the back-end user executing an explicit command to save and/or deploy the configurations instructed via the back-end GUI.

At block 616, in some embodiments, the system may receive a third user input comprising an instruction for defining an order for a plurality of natural-language statements, wherein one of the natural-language statements of the plurality of natural-language statements is associated with the visual representation of the natural-language statement structure. In some embodiments, a user of the back-end GUI may execute an input specifying an order of statements (e.g., an order of sentences) that may together form a paragraph for storage as a note into an electronic medical record. In some embodiments, the back-end user may assign a name to a natural-language statement structure being defined such that the name of the statement structure may be able to be used as a label for specifying a placement or order of a statement generated in accordance with that structure.

It should be noted that ordinal numbers used to refer to features in exemplary method 600 may be the same or different from ordinal numbers used elsewhere in the disclosure and/or in the claims to refer to features that share one or more characteristics in common with said features in exemplary method 600.

Figure 7:
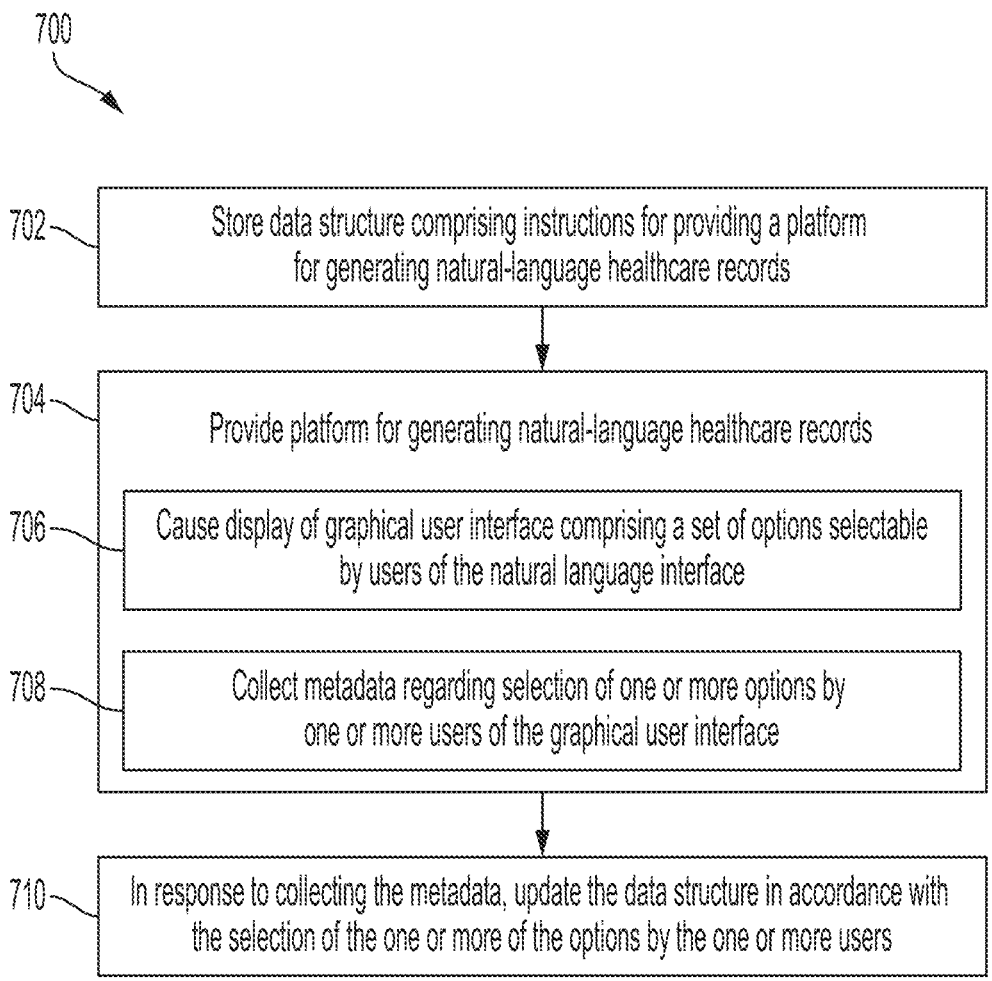
FIG. 7 depicts a flow chart describing a method for configuring a natural-language medical record generation platform, in accordance with some embodiments.

FIG. 7 depicts a flow chart describing method 700 for providing a system for configuring a natural-language medical record generation platform, in accordance with some embodiments. In some embodiments, method 700 may be performed by a system for providing a natural-language medical record generation platform, such as system 100 described above with reference to FIG. 1. As described below, method 700 may include providing an interface for executing inputs regarding patient information, collecting metadata regarding usage of said interface, and updating configuration of said interface based on the collected metadata. For example, options regarding symptoms or other patient medical information may be added to or removed from the interface based on metadata regarding whether, when, and/or in what manner various options have been selected in the past. In some embodiments, method 700 may be performed by a system providing a front-end user interface such as GUI 200 and/or GUI 400.

At block 702, in some embodiments, the system may store a data structure comprising instructions for providing a platform for generating natural-language healthcare records. In some embodiments, the data structure may be a data structure a complaint data structure stored in or in association with the system, and the complaint data structure may be configured by a back-end user of a back-end GUI in order to configure the system to provide a front-end GUI for entering medical information for patients presenting with the complaint. The complaint data structure may be configured in accordance with one or more of the techniques described herein, for example method 600 and/or for example using a back-end GUI such as GUI 500.

At block 704, in some embodiments, the system may provide a platform for generating natural-language healthcare records in accordance with the instructions. For example, the system may execute the instructions in order to cause the system to display an interface, such as a front-end graphical user interface, for collecting medical information regarding a patient and for automatically generating one or more natural-language statements based on said inputs. The front-end GUI may, in some embodiments, be GUI 200 and/or GUI 400.

At block 706, in some embodiments, providing the platform for generating natural-language healthcare records comprises causing display of a graphical user interface comprising a set of options selectable by users of the natural language interface. For example, as discussed herein, the front-end graphical user interface may display one or more selectable and/or deselectable icons that front-end users may interact with in order to specify patient medical information to be used in generating a natural-language statement for entry into an electronic medical record.

At block 708, in some embodiments, providing the platform for generating natural-language healthcare records comprises collecting metadata regarding selection of one or more options by one or more users of the graphical user interface. For example, the system may in some embodiments collect metadata (e.g., anonymized metadata) regarding whether, when, in what manner, in what contexts, and/or how frequently one or more options is selected by one or more front-end users. For example, the system may be configured to track how often certain options are selected for certain demographic subsets of patients; and/or how often certain options are selected by certain doctors; how often certain options are selected at certain facilities or in certain regions; how often certain options are selected in connection with an indication of certain complaints, symptoms, contextual information, medical history, or other relevant medical information.

At block 710, in some embodiments, the system may, in response to collecting the metadata, update the data structure in accordance with the selection of the one or more of the options by the one or more users. By collecting metadata regarding how and when certain options are selected by front-end users, the system may be able to glean insights regarding how the platform can be updated to be more usable, more efficient, more accurate, and/or more medically relevant. The system may be configured, for example, to add one or more options to a complaint template (or to promote said one or more options by displaying them more prominently) in accordance with frequent selection by one or more front end users using the complaint template; on the other hand, the system may be configured to remove one or more options from a complaint template (or to demote said one or more options by displaying them less prominently) in accordance with infrequent selection by one or more front end users using the complaint template. The system may be configured to make subtle adjustments to one or more complaint templates such that the system is configured to respond dynamically to front-end user interfaces in order to (prominently) display those options to the front-end user that are determined, based on metadata previously collected and analyzed, to be most likely to be selected by the front-end user based on front-end user information already entered by the user or otherwise known to the system, including patient information, demographic information, location information, and/or complaint/symptom/medical information.

In some embodiments, alternately or additionally to updating a complaint template to include or exclude one or more options based on metadata collection, the system may be configured to, based on metadata collection, generate a new complaint template, delete a complaint template, add a complaint-element to a complaint template, remove a complaint-element to a complaint template, add a data item to a dataset, and/or remove a data item from a dataset.

In some embodiments, changes to system configurations based on metadata may be automatically implemented by the system. In some embodiments, a back-end user (e.g., a user of GUI 500) may be prompted by the system to confirm changes to system configurations suggested based on metadata.

Figure 8:
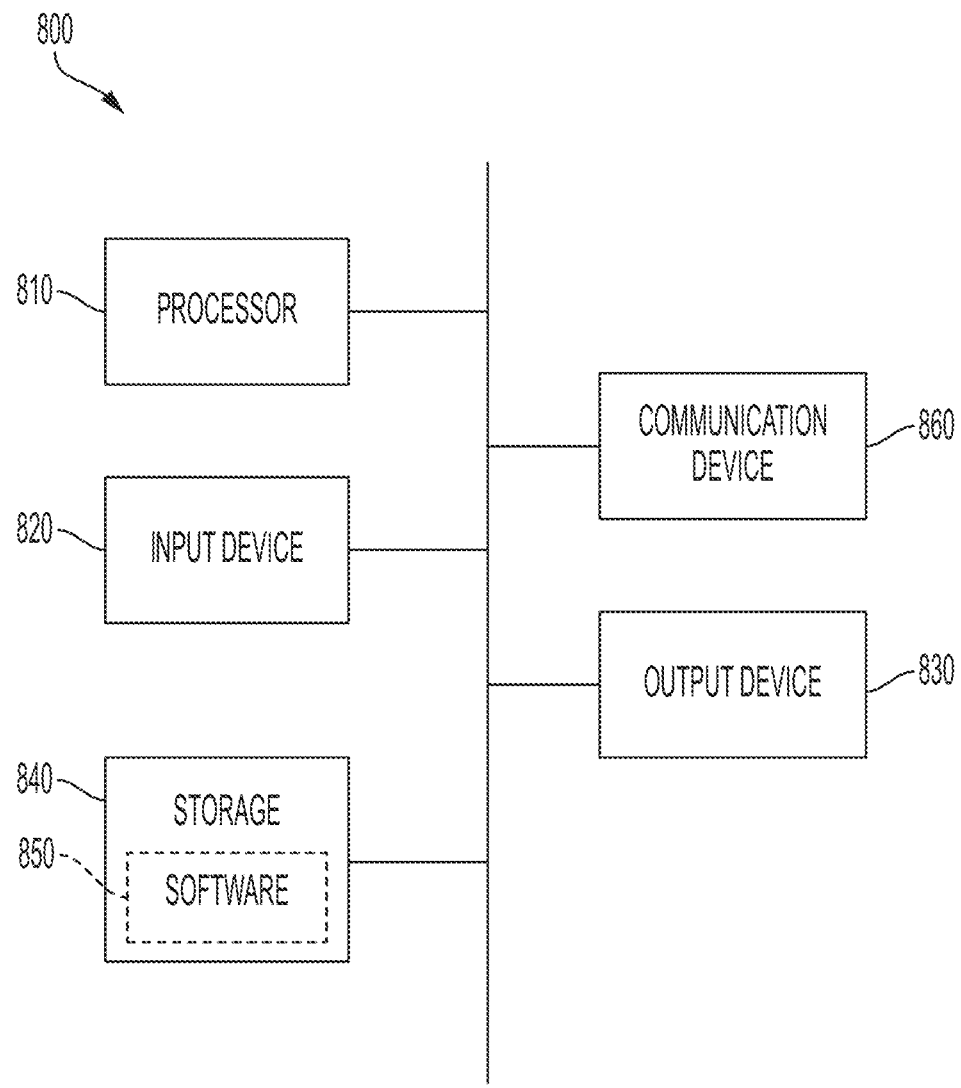
FIG. 8 depicts a computer, in accordance with some embodiments.

FIG. 8 illustrates an example of a computer, according to some embodiments. Computer 800 can be a component of a bioelectrical sensor system according to the systems and methods described above, such as system 100 of FIG. 1. In some embodiments, computer 800 may execute a method for automatically generating natural-language entries for electronic health records and/or for configuring systems and graphical user interfaces for automatically generating natural-language entries for electronic health records.

Computer 800 can be a host computer connected to a network. Computer 800 can be a client computer or a server. As shown in FIG. 8, computer 800 can be any suitable type of microprocessor-based device, such as a personal computer, workstation, server, or handheld computing device, such as a phone or tablet. The computer can include, for example, one or more of processor 810, input device 820, output device 830, storage 840, and communication device 860. Input device 820 and output device 830 can correspond to those described above and can either be connectable or integrated with the computer.

Input device 820 can be any suitable device that provides input, such as a touch screen or monitor, keyboard, mouse, or voice-recognition device. Output device 830 can be any suitable device that provides an output, such as a touch screen, monitor, printer, disk drive, or speaker.

Storage 840 can be any suitable device that provides storage, such as an electrical, magnetic, or optical memory, including a random access memory (RAM), cache, hard drive, CD-ROM drive, tape drive, or removable storage disk. Communication device 860 can include any suitable device capable of transmitting and receiving signals over a network, such as a network interface chip or card. The components of the computer can be connected in any suitable manner, such as via a physical bus or wirelessly. Storage 840 can be a non-transitory computer-readable storage medium comprising one or more programs, which, when executed by one or more processors, such as processor 810, cause the one or more processors to execute methods described herein.

Software 850, which can be stored in storage 840 and executed by processor 810, can include, for example, the programming that embodies the functionality of the present disclosure (e.g., as embodied in the systems, computers, servers, and/or devices as described above). In some embodiments, software 850 can include a combination of servers such as application servers and database servers.

Software 850 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include but is not limited to, an electronic, magnetic, optical, electromagnetic, or infrared wired or wireless propagation medium.

Computer 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 800 can implement any operating system suitable for operating on the network. Software 850 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The following is a non-limiting list of embodiments, any of which may be combined in whole or in part with one another and/or in whole or in part with any other aspects or features disclosed herein:

1. A system for generating a natural-language statement for a healthcare record, the system comprising one or more processors configured to cause the system to:
   display a graphical user interface comprising a canvas region and a menu region, wherein menu region comprises a first set of one or more interactive graphical user interface menu objects configured to receive user inputs corresponding to medical information; and
   receive data representing a first user input comprising user interaction with one or more of the first set of menu objects, the first input indicating medical information for a patient;
   in accordance with the first user input:
      generate a natural-language statement based on the medical information indicated by the first user input; and
      update display of the canvas region to display the natural-language statement.
2. The system of embodiment 1, wherein generating the natural-language statement based on the medical information indicated by the first user input comprises inserting a text string associated with the indicated medical information into a predefined syntactical structure.
3. The system of any one of embodiments 1-2, wherein the natural-language statement is generated based on the first input and based on one or more additional inputs indicating additional medical information for the patient.
4. The system of any one of embodiments 1-3, wherein one or more processors configured to cause the system to store data representing a healthcare record, the data comprising the generated natural-language statement.
5. The system of any one of embodiments 1-4, wherein:
   the menu region comprises a second set of one or more menu objects configured to receive user inputs corresponding to demographic information;
   the one or more processors are configured to cause the system to receive data representing a second user input comprising user interaction with one or more of the second plurality of menu objects, the second input indicating patient demographic information for the patient; and
   generating the natural language statement is performed in accordance with the second user input.
6. The system of any one of embodiments 1-5, wherein:
   the menu region comprises a third set of one or more menu objects configured to receive user inputs corresponding to complaint information;
   the one or more processors are configured to cause the system to receive data representing a third user input comprising user interaction with one or more of the third plurality of menu objects, the third input indicating complaint information for the patient; and
   wherein the first set of one or more menu objects are selected by the system for display in the interface based on the complaint information indicated by the third input.
7. The system of embodiment 6, wherein selecting the first set of one or more menu objects comprises selecting from among a plurality of predetermined sets of one or more menu objects, each of the plurality of sets of one or more menu objects corresponding to a different respective complaint.
8. The system of any one of embodiments 6-7, wherein selecting the first set of one or more menu objects is performed on the basis of indication by a user of one or more of a specialty, a healthcare system, a payer, and a clinician.
9. The system of any one of embodiments 1-8, wherein:
   the first set of one or more menu objects comprises a first subset of menu objects, wherein each of the menu objects of the first subset represents a respective potential symptom; and
   the first input comprises a selection of one or more of the menu objects of the first subset representing a symptom of the patient.
10. The system of any one of embodiments 1-9, wherein:
    the first set of one or more menu objects comprises a second subset of menu objects, wherein each of the menu objects of the second subset represents a respective potential symptom onset characterization; and
    the first input comprises a selection of one or more of the menu objects of the second subset representing a symptom onset characterization of the patient.
11. The system of any one of embodiments 1-10, wherein:
    the first set of one or more menu objects comprises a third subset of menu objects, wherein each of the menu objects of the third subset represents a respective potential symptom timing information; and
    the first input comprises a selection of one or more of the menu objects of the third subset representing symptom timing information of the patient.
12. The system of any one of embodiments 1-11, wherein:
    the first set of one or more menu objects comprises a fourth subset of menu objects, wherein each of the menu objects of the fourth subset represents a respective potential symptom frequency; and
    the first input comprises a selection of one or more of the menu objects of the fourth subset representing a symptom frequency of the patient.
13. The system of any one of embodiments 1-12, wherein:
    the first set of one or more menu objects comprises a fifth subset of menu objects, wherein each of the menu objects of the fifth subset represents a respective potential symptom locations; and
    the first input comprises a selection of one or more of the menu objects of the fifth subset representing a symptom location of the patient.
14. The system of any one of embodiments 1-13, wherein:
    the first set of one or more menu objects comprises a sixth subset of menu objects, wherein each of the menu objects of the sixth subset represents a respective potential contextual information; and
    the first input comprises a selection of one or more of the menu objects of the sixth subset representing contextual information of the patient.
15. The system of any one of embodiments 1-14, wherein:
    the first set of one or more menu objects comprises a seventh subset of menu objects, wherein each of the menu objects of the seventh subset represents a respective potential symptom quality; and
    the first input comprises a selection of one or more of the menu objects of the seventh subset representing a symptom quality of the patient.

16. The system of any one of embodiments 1-15, wherein:
    the first set of one or more menu objects comprises an eighth subset of menu objects, wherein each of the menu objects of the eighth subset represents a respective potential prior medical condition; and
    the first input comprises a selection of one or more of the menu objects of the eighth subset representing a prior medical condition of the patient.
17. The system of any one of embodiments 1-16, wherein:
    the first set of one or more menu objects comprises a ninth subset of menu objects, wherein each of the menu objects of the ninth subset represents a respective potential current medication; and
    the first input comprises a selection of one or more of the menu objects of the ninth subset representing a current medication of the patient.
18. The system of any one of embodiments 1-17, wherein:
    the first set of one or more menu objects comprises a tenth subset of menu objects, wherein each of the menu objects of the tenth subset represents a respective potential medication to be prescribed; and
    the first input comprises a selection of one or more of the menu objects of the tenth subset representing a medication to be prescribed for the patient.
19. The system of any one of embodiments 1-18, wherein:
    the first set of one or more menu objects comprises an eleventh subset of menu objects, wherein each of the menu objects of the eleventh subset represents a respective potential treatment to be prescribed; and
    the first input comprises a selection of one or more of the menu objects of the eleventh subset representing a treatment to be prescribed for the patient.
20. The system of any one of embodiments 1-19, wherein:
    the first set of one or more menu objects comprises a first field configured to accept entry of character strings;
    the first input comprises entry of a first character string into the first field; and
    generating the natural-language statement based on the medical information indicated by the first user input comprises inserting the character string into a predetermined natural-language sentence structure.
21. The system of any one of embodiments 1-20, wherein:
    the first set of one or more menu objects comprises a second field configured to accept entry of character strings;
    the first input comprises entry of a second character string into the second field; and
    generating the natural-language statement based on the medical information indicated by the first user input comprises inserting the character string into a predetermined natural-language paragraph structure as a complete sentence.
22. The system of any one of embodiments 1-21, wherein the one or more processors are configured to cause the system to, in accordance with the first user input, dynamically update the menu region.
23. The system of any one of embodiments 1-22, wherein the one or more processors are configured to cause the system to:
    detect a fourth user input comprising an instruction to manually modify the natural-language statement displayed in the canvas region;
    in response to detecting the fourth user input, update the displayed natural-language statement displayed in the canvas region.
24. The system of any one of embodiments 1-23, wherein:
    displaying the natural-language statement in the canvas region comprises displaying the natural-language statement using a first format; and
    the one or more processors are configured to cause the system to display a review screen on which the natural-language statement is displayed using a second format.
25. The system of any one of embodiments 1-24, wherein the one or more processors are configured to cause the system to capture and store metadata representing the first input.
26. The system of any one of embodiments 1-25, wherein updating display of the canvas region to display the natural-language statement is performed automatically in response to detection of the first user input.
27. The system of any one of embodiments 1-26, wherein the system is configured such that only one menu object of the first set of menu objects are able to be selected at once.
28. The system of any one of embodiments 1-27, wherein the system is configured such that multiple menu objects of the first set of menu objects are able to be selected at once.
29. The system of any one of embodiments 1-28, wherein the system is configured such that one or more of the menu objects is able to be toggled between two or more states selected from: positively indicated, negatively indicated, neither positively nor negatively indicated.
30. A non-transitory computer-readable storage medium storing instructions for generating a natural-language statement for a healthcare record, the instructions configured to be executed by a system comprising one or more processors to cause the system to:
    display a graphical user interface comprising a canvas region and a menu region, wherein menu region comprises a first set of one or more interactive graphical user interface menu objects configured to receive user inputs corresponding to medical information; and
    receive data representing a first user input comprising user interaction with one or more of the first set of menu objects, the first input indicating medical information for a patient;
    in accordance with the first user input:
        generate a natural-language statement based on the medical information indicated by the first user input; and
        update display of the canvas region to display the natural-language statement.
31. A method for generating a natural-language statement for a healthcare record, the method performed at a system comprising one or more processor, the method comprising:
    displaying a graphical user interface comprising a canvas region and a menu region, wherein menu region comprises a first set of one or more interactive graphical user interface menu objects configured to receive user inputs corresponding to medical information; and
    receiving data representing a first user input comprising user interaction with one or more of the first set of menu objects, the first input indicating medical information for a patient;
    in accordance with the first user input:
        generating a natural-language statement based on the medical information indicated by the first user input; and updating display of the canvas region to display the natural-language statement.

32. A system for configuring a medical record generation platform, the system comprising one or more processors configured to cause the system to:
    display a first graphical user interface comprising a visual representation of a natural-language statement structure;
    receive a first input comprising an instruction to update the natural-language statement structure to specify a first aspect of patient medical information;
    in response to receiving the first input:
        update display of the visual representation of the natural-language statement to include a visual representation of the first aspect of patient medical information;
        display an option group region configured to represent a first set of options for describing the first aspect of patient medical information;
    in accordance with the first user input, store a data structure comprising instructions for providing a platform for generating a natural-language healthcare document conforming to the natural-language statement structure represented by the visual representation, wherein the natural-language statement specifies the first aspect of patient medical information.

33. The system of embodiment 32, wherein:
    the one or more processors are configured to cause the system to:
        receive a second input comprising an instruction to add a first option to the first set of options; and
        in response to receiving the second user input, display a graphical user interface object representing the first option in the option group region; and
    storing the data structure is performed in accordance with the second user input, such that the instructions are configured for allowing selection of the first option such that selection of the first option specifies the first aspect of patient medical information for inclusion in the generated natural-language healthcare record.

34. The system of any one of embodiments 32-33, wherein providing the platform for generating the natural-language healthcare record comprises:
    causing display of a second graphical user interface comprising a canvas region and a menu region;
    receiving data representing a third input executed against the second graphical user interface, wherein the third input specifies the first aspect of patient medical information for a given patient;
    in response to receiving the third user input, generating and displaying a natural-language statement, based on the specified first aspect of patient medical information for the given patient, and conforming to the natural-language statement structure specified by the first input.

35. The system of any one of embodiments 32-34, wherein first input comprises an instruction to configure the set of options in the option group such that a single one of the options may be selected to indicate the first aspect of patient medical information for inclusion in the natural-language healthcare record.

36. The system of any one of embodiments 32-35, wherein first input comprises an instruction to configure the set of options in the option group such that multiple options of the options may be selected to indicate the first aspect of patient medical information for simultaneous inclusion in the natural-language record.

37. The system of any one of embodiments 32-36, wherein the first aspect of patient medical information comprises an indication of a symptom.

38. The system of any one of embodiments 32-37, wherein the first aspect of patient medical information comprises an indication of an onset mode of a symptom.

39. The system of any one of embodiments 32-38, wherein the first aspect of patient medical information comprises an indication of onset timing of a symptom.

40. The system of any one of embodiments 32-39, wherein the first aspect of patient medical information comprises an indication of a frequency.

41. The system of any one of embodiments 32-40, wherein the first aspect of patient medical information comprises an indication of a location of a symptom.

42. The system of any one of embodiments 32-41, wherein the first aspect of patient medical information comprises contextual information.

43. The system of any one of embodiments 32-42, wherein the first aspect of patient medical information comprises an indication of a quality of a symptom.

44. The system of any one of embodiments 32-43, wherein the first aspect of patient medical information comprises an indication of a prior medical condition.

45. The system of any one of embodiments 32-44, wherein the first aspect of patient medical information comprises an indication of a current medication.

46. The system of any one of embodiments 32-45, wherein the first aspect of patient medical information comprises an indication of a medication to be prescribed.

47. The system of any one of embodiments 32-46, wherein the first aspect of patient medical information comprises an indication of a treatment to be prescribed.

48. The system of any one of embodiments 32-47, wherein the first aspect of patient medical information comprises an indication of lab test results.

49. The system of any one of embodiments 32-48, wherein the first aspect of patient medical information comprises an indication of a lab test to be ordered.

50. The system of any one of embodiments 32-49, wherein the first aspect of patient medical information comprises an indication of imaging procedure results.

51. The system of any one of embodiments 32-50, wherein the first aspect of patient medical information comprises an indication of an imaging procedure to be ordered.

52. The system of any one of embodiments 32-51, wherein the first aspect of patient medical information comprises an indication of an organ system.

53. The system of any one of embodiments 32-52, wherein the first aspect of patient medical information comprises an indication of a diagnostic procedure.

54. The system of any one of embodiments 32-53, wherein the first aspect of patient medical information comprises an indication of a diagnosis.

55. The system of any one of embodiments 32-54, wherein the one or more processors are configured to cause the system to receive a fourth input comprising instructions for defining an order for a plurality of natural-language statements, wherein one of the natural-language statements of the plurality of natural-language statements is associated with the visual representation of the natural-language statement structure.

56. The system of any one of embodiments 55, wherein the fourth input comprises a respective name to be associated with one or more of the natural language statements.

57. A non-transitory computer-readable storage medium storing instructions for configuring a medical record generation platform, the instructions configured to be executed by a system comprising one or more processors to cause the system to:
    display a first graphical user interface comprising a visual representation of a natural-language statement structure;
    receive a first input comprising an instruction to update the natural-language statement structure to specify a first aspect of patient medical information;
    in response to receiving the first input:
        update display of the visual representation of the natural-language statement to include a visual representation of the first aspect of patient medical information;
        display an option group region configured to represent a first set of options for describing the first aspect of patient medical information;
    in accordance with the first user input, store a data structure comprising instructions for providing a platform for generating a natural-language healthcare document conforming to the natural-language statement structure represented by the visual representation, wherein the natural-language statement specifies the first aspect of patient medical information.

58. A method for configuring a medical record generation platform, the method performed at a system comprising one or more processors, the method comprising:
    display a first graphical user interface comprising a visual representation of a natural-language statement structure;
    receive a first input comprising an instruction to update the natural-language statement structure to specify a first aspect of patient medical information;
    in response to receiving the first input:
        update display of the visual representation of the natural-language statement to include a visual representation of the first aspect of patient medical information;
        display an option group region configured to represent a first set of options for describing the first aspect of patient medical information;
    in accordance with the first user input, store a data structure comprising instructions for providing a platform for generating a natural-language healthcare document conforming to the natural-language statement structure represented by the visual representation, wherein the natural-language statement specifies the first aspect of patient medical information.

59. A system for configuring a medical record generation platform, the system comprising one or more processors configured to cause the system to:
    store a data structure comprising instructions for providing a platform for generating natural-language healthcare records, wherein providing the platform comprises:
        causing display of a graphical user interface comprising a set of options selectable by users of the graphical user interface; and
        collecting metadata regarding selection of one or more of the options by a plurality of users; and
        in response to collecting the metadata, update the data structure in accordance with the selection of the one or more of the options by the plurality of users.

60. The system of embodiment 59, wherein updating the data structure comprises removing one of the options from the set of options.

61. The system of any one of embodiments 59-60, wherein updating the data structure comprises adding an option to the set of options.

62. The system of any one of embodiments 59-61, wherein the options in the set of options are selectable to configure natural-language statements in the natural-language records.

63. The system of any one of embodiments 59-62, wherein the options in the set of options correspond to medications to be prescribed for a patient.

64. The system of any one of embodiments 59-63, wherein the options in the set of options correspond to treatments to be prescribed for a patient.

65. The system of any one of embodiments 59-64, wherein the options in the set of options correspond to symptoms reported by a patient.

66. A non-transitory computer-readable storage medium storing instructions for configuring a medical record generation platform, the instructions configured to be executed by a system comprising one or more processors to cause the system to:
    store a data structure comprising instructions for providing a platform for generating natural-language healthcare records, wherein providing the platform comprises:
        causing display of a graphical user interface comprising a set of options selectable by users of the graphical user interface; and
        collecting metadata regarding selection of one or more of the options by a plurality of users; and
        in response to collecting the metadata, update the data structure in accordance with the selection of the one or more of the options by the plurality of users.

67. A method for configuring a medical record generation platform, the method performed at a system comprising one or more processors, the method comprising:
    storing a data structure comprising instructions for providing a platform for generating natural-language healthcare records, wherein providing the platform comprises:
        causing display of a graphical user interface comprising a set of options selectable by users of the graphical user interface; and
        collecting metadata regarding selection of one or more of the options by a plurality of users; and
        in response to collecting the metadata, updating the data structure in accordance with the selection of the one or more of the options by the plurality of users.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A system for configuring a medical record generation platform, the system comprising one or more processors configured to cause the system to:
    display a first graphical user interface (GUI) comprising a visual representation of a natural-language statement structure;
    receive a first input comprising an instruction to update the natural-language statement structure to specify a first aspect of patient medical information;
    in response to receiving the first input:
        update display of the visual representation of the natural-language statement structure to include a visual representation of the first aspect of patient medical information;
        display an option group region associated with the visual representation of the first aspect of patient medical information and comprising a first set of options for describing the first aspect of patient medical information;
    receive a second input comprising a selection of one or more of the options in the first set of options;
    in accordance with the first user input, store a data structure comprising instructions for providing a platform configured to cause display of a second GUI for generating a healthcare record comprising a natural-language statement conforming to the updated natural-language statement structure represented by the visual representation of the natural-language statement structure, wherein the natural-language statement generated using the second GUI specifies the first aspect of patient medical information,
    wherein the second GUI comprises a set of one or more options configured in accordance with the one or more options selected via the first GUI, and wherein the second GUI is configured such that the natural-language statement is generated in accordance with a selection made via the second GUI from the set of one or more options.

2. The system of claim 1, wherein:
    the one or more processors are configured to cause the system to:
        receive a third input comprising an instruction to add a first option to the first set of options; and
        in response to receiving the third user input, display a graphical user interface object representing the first option in the option group region; and
    storing the data structure is performed in accordance with the third user input, such that the instructions are configured for allowing selection of the first option to specify the first aspect of patient medical information for inclusion in the generated healthcare record.

3. The system of claim 1, wherein providing the platform configured to cause display of the second GUI for generating the healthcare record comprises:
    causing display of the second GUI comprising a canvas region and a menu region;
    receiving data representing a first input executed against the second GUI, wherein the first input executed against the second GUI specifies the first aspect of patient medical information for a given patient;
    in response to receiving the first user input executed against the second GUI, generating and displaying a natural-language statement based on the specified first aspect of patient medical information for the given patient and conforming to the natural-language statement structure updated based on the instruction of the first input received at the first GUI.

4. The system of claim 1, wherein the first input comprises an instruction to configure the first set of options in the option group region such that a single one of the options may be selected to indicate the first aspect of patient medical information for inclusion in the natural-language healthcare record.

5. The system of claim 1, wherein the first input comprises an instruction to configure the first set of options in the option group region such that multiple options of the options may be selected to indicate the first aspect of patient medical information for simultaneous inclusion in the natural-language healthcare record.

6. The system of claim 1, wherein the first aspect of patient medical information comprises an indication of a symptom.

7. The system of claim 1, wherein the first aspect of patient medical information comprises an indication of an onset mode of a symptom.

8. The system of claim 1, wherein the first aspect of patient medical information comprises an indication of onset timing of a symptom.

9. The system of claim 1, wherein the first aspect of patient medical information comprises an indication of a frequency.

10. The system of claim 1, wherein the first aspect of patient medical information comprises an indication of a location of a symptom.

11. The system of claim 1, wherein the first aspect of patient medical information comprises contextual information.

12. The system of claim 1, wherein the first aspect of patient medical information comprises an indication of a quality of a symptom.

13. The system of claim 1, wherein the first aspect of patient medical information comprises an indication of a prior medical condition.

14. The system of claim 1, wherein the first aspect of patient medical information comprises an indication of a current medication.

15. The system of claim 1, wherein the first aspect of patient medical information comprises an indication of a medication to be prescribed.

16. The system of claim 1, wherein the first aspect of patient medical information comprises an indication of a treatment to be prescribed.

17. The system of claim 1, wherein the first aspect of patient medical information comprises an indication of lab test results.

18. The system of claim 1, wherein the first aspect of patient medical information comprises an indication of a lab test to be ordered.

19. The system of claim 1, wherein the first aspect of patient medical information comprises an indication of imaging procedure results.

20. The system of claim 1, wherein the first aspect of patient medical information comprises an indication of an imaging procedure to be ordered.

21. The system of claim 1, wherein the first aspect of patient medical information comprises an indication of an organ system.

22. The system of claim 1, wherein the first aspect of patient medical information comprises an indication of a diagnostic procedure.

23. The system of claim 1, wherein the first aspect of patient medical information comprises an indication of a diagnosis.

24. The system of claim 1, wherein the one or more processors are configured to cause the system to receive a fourth input comprising instructions for defining an order for a plurality of natural-language statements, wherein one of the natural-language statements of the plurality of natural-language statements is associated with the visual representation of the natural-language statement structure.

25. The system of claim 24, wherein the fourth input comprises a respective name to be associated with one or more of the natural language statements.

26. A non-transitory computer-readable storage medium storing instructions for configuring a medical record generation platform, the instructions configured to be executed by a system comprising one or more processors to cause the system to:
  display a first graphical user interface (GUI) comprising a visual representation of a natural-language statement structure;
  receive a first input comprising an instruction to update the natural-language statement structure to specify a first aspect of patient medical information;
  in response to receiving the first input:
    update display of the visual representation of the natural-language statement structure to include a visual representation of the first aspect of patient medical information;
    display an option group region associated with the visual representation of the first aspect of patient medical information and comprising a first set of options for describing the first aspect of patient medical information;
  receive a second input comprising a selection of one or more of the options in the first set of options;
  in accordance with the first user input, store a data structure comprising instructions for providing a platform configured to cause display of a second GUI for generating a healthcare record comprising a natural-language statement conforming to the updated natural-language statement structure represented by the visual representation of the natural-language statement structure, wherein the natural-language statement generated using the second GUI specifies the first aspect of patient medical information,
  wherein the second GUI comprises a set of one or more options configured in accordance with the one or more options selected via the first GUI, and wherein the second GUI is configured such that the natural-language statement is generated in accordance with a selection made via the second GUI from the set of one or more options.

27. A method for configuring a medical record generation platform, the method performed at a system comprising one or more processors, the method comprising:
  displaying a first graphical user interface (GUI) comprising a visual representation of a natural-language statement structure;
  receiving a first input comprising an instruction to update the natural-language statement structure to specify a first aspect of patient medical information;
  in response to receiving the first input:
    updating display of the visual representation of the natural-language statement structure to include a visual representation of the first aspect of patient medical information;
    displaying an option group region associated with the visual representation of the first aspect of patient medical information and comprising a first set of options for describing the first aspect of patient medical information;
  receiving a second input comprising a selection of one or more of the options in the first set of options;
  in accordance with the first user input, storing a data structure comprising instructions for providing a platform configured to cause display of a second GUI for generating a healthcare record comprising a natural-language statement conforming to the updated natural-language statement structure represented by the visual representation of the natural-language statement structure, wherein the natural-language statement generated using the second GUI specifies the first aspect of patient medical information,
  wherein the second GUI comprises a set of one or more options configured in accordance with the one or more options selected via the first GUI, and wherein the second GUI is configured such that the natural-language statement is generated in accordance with a selection made via the second GUI from the set of one or more options.

* * * * *